United States Patent [19]
Mattson

[11] Patent Number: 5,830,910
[45] Date of Patent: Nov. 3, 1998

[54] CYTOCHALASINS USEFUL IN PROVIDING PROTECTION AGAINST NERVE CELL INJURY ASSOCIATED WITH NEURODEGENERATIVE DISORDERS

[75] Inventor: Mark P. Mattson, Lexington, Ky.

[73] Assignee: University of Kentucky Research Foundation, Lexington, Ky.

[21] Appl. No.: 546,745

[22] Filed: Oct. 23, 1995

[51] Int. Cl.$^6$ .................................................. A61K 31/40
[52] U.S. Cl. ............................................................ 514/411
[58] Field of Search ............................................ 514/411

[56] References Cited

PUBLICATIONS

Baines, A.J. In: R.D. Burgoyne (ed) *The Neuronal Cytoskeleton*. Wiley–Liss, New York, pp. 161–193 (1991).
Bamburg, J.R., & Bernstein, B.W. In: R.D. Burgoyne (ed) *The Neuronal Cytoskeleton*. Wiley–Liss, New York, pp. 121–160 (1991).
Bear, M.F. & Malenka, R.C. *Curr. Opin. Neurobiol.* 4, 389–399 (1994).
Bencherif, M., & Lukas, R.J. *J. Neurochem.* 61, 852–864 (1993).
Bonventre, J.V., Phospholipase A$_2$ and signal transduction. *J. Am. Soc. Nephrol.* 3:128–150; 1992.
Choi, D.W. *Neuron* 1, 623–634 (1988).
DeBoni, U. et al., Controlled induction of paired helical filaments of the Alzheimer type in cultured human neurons, by glutamate and aspartate. *J. Neurol. Sci.* 68:105–118; 1985.
DeLorenzo, R.J., Antiepileptic Drugs, Third Edition; Raven Press, Ltd., 1989.
Elliott, E.M. et al., Corticosterone exacerbates kainate–induced alterations in hippocampal tau immunoreactivity and spectrin proteolysis in vivo. *J. Neurochem.* 61:57–67; 1993.
Goodman, Y. et al., Secreted forms of βAPP protect hippocampal neurons against Aβ toxicity and oxidative injury. *Soc. Neurosci. Abstr.*, 19:1251; 1993.
Haass, C. et al., Amyloid β–peptide is produced by cultured cells during normal metabolism. *Nature* 359:322–325; 1992.
Hope, W.C. et al., In vitro inhibition of the biosynthesis of slow reacting substance of anaphylaxis (SRS–A) and lipoxygenase activity by quercetin. *Biochem. Pharmacol.* 32: 367–371; 1983.
Kase, H., Iwahashi, K., Nakanishi, S., Matsuda, Y., Yamada, K., Takahishi, J., Murakata, C., Sato, A., and Kaneko, M., K–252 compounds, novel and potent inhibitors of protein kinase C and cyclic nucleotide–dependent protein kinases. *Biochem. Biophys. Res. Commun.* 142:436–440; 1987.
Kelly, R.B. *Cell/Neuron* 72/10 (Suppl), 43–53 (1993).
Khachaturian, Z.S., The role of calcium regulation in brain agina: reexamination of a hypothesis. *Aging* 1:17–34; 1989.
Kosik, K.S. et al., Epitopes that span the tau molecule are shared with paired helical filaments. *Neuron* 1:817–825; 1988.
Marsh, L., & Letournea, P.C. *J. Cell. Biol.* 99, 2041–2047 (1984).

Mattson, M.P., Kumar, K., Cheng, B., Wang, H., and Michaelis, E.K., Basic FGF regulates the expression of a functional 71 kDa NMDA receptor protein that mediates calcium influx and neurotoxicity in cultured hippocampal neurons. *J. Neurosci.* 13:4575–4588, 1993.
Mohr, E. et al., GABA–Agonist therapy for Alzheimer's Disease. *Clinical Neuropharmacology* 9:257–263; 1986.
Nadler, I.V., & Cuthbertson, G.J. *Brain Res.* 195, 47–56 (1980).
Nowak, T.S. Jr. et al., Stress protein and proto–oncogene expression as indicators of neuronal pathophysiology after ischemia. *Prog. Brain Res.* 96:195–208; 1993.
Perry, G. et al., Ubiquitin is detected in neurofibrillary tangles and senile plaque neurites of Alzheimer's disease. *Proc. Natl. Acad. Sci. U.S.A.* 84:3030–3036; 1987.
Rayevsky, K.S. et al., GABA–ergic drugs: effects on conditioning, memory, and learning. *Pharmacol. Res. Commun.* 15:85–96; 1983.
Rose, K. et al., Nordihydroguaiaretic acid potentiates rapidly triggered excitotoxic injury in murine cortical cell cultures. *Soc. Neurosci. Abstr.* 17:784; 1991.
Rothman, S., & Olney, J.W. *Ann. Neurol.* 19, 105–111 (1986).
Sapolsky, R.M. et al., The Neuroendocrinology of Stress and Aging: The Glucocorticoid Cascade Hypothesis, *Endocrine Reviews*, vol. 7, No. 3, pp. 284–301 (1986).
Shoji, J. et al., Production of the Alzheimer amyloid β protein by normal proteolytic processing. *Science* 258:126–129; 1992.
Simmons, L.K. et al., Secondary structure of amyloid β peptide correlates with neurotoxic activity in vitro. *Mol. Pharmacol.* 1994, In press.
Smith, et al., Excess brain protein oxidation and enxyme dysfunction in normal aging and in Alzheimer disease. *Proc. Natl. Acad. Sci. U.S.A.* 88:10540–10543; 1991.
Sternlicht, H., & Ringel, I., *J. Biol. Chem.* 254, 10540–10550 (1979).
Watanabe, Y. et al., Phenytoin prevents stress and corticosterone–induced atrophy of CA3 pyramidal neurons. *Hippocampus* 2:431–435; 1992.
Wolozin, B.L. et al., A neuronal antigen in the brains of Alzheimer's patients. *Science* 232:648–650; 1986.
Arispe, N. et al., Alzheimer disease amyloid β protein forms calcium channels in bilayer membranes: Blockade by tromethamine and aluminum. *Proc. Natl. Acad. Sci. USA* 90:567–571; 1993.
Bading, H. et al., Stimulation of protein tyrosine phosphorylation by NMDA receptor activation. *Science* 253:912–914; 1991.

(List continued on next page.)

*Primary Examiner*—William R. A. Jarvis
*Attorney, Agent, or Firm*—Lowe, Price, Leblanc & Becker

[57] ABSTRACT

The present invention relates to novel therapeutic uses of certain compounds to protect nerve cells from injury and death. The compounds include cytochalasin D and related analogs, and cytochalasin E and related analogs.

6 Claims, 15 Drawing Sheets

OTHER PUBLICATIONS

Behl, C. et al., Vitamin E protects nerve cells for amyloid β protein toxicity. *Biochem. Biophys. Res. Commun.* 186:944–950; 1992.

Bleck, T.P., Convulsive disorders: status epilepticus. *Clin. Neuropharmacol.* 14:191–198; 1991.

Boxer, P.A. et al., Comparison of phenytoin with noncompetitive N–methyl–D–aspartate antagonists in a model of focal brain ischemia in rat. *Stroke* 21:III47–III51; 1990.

Breitner, J.C.S. et al., Inverse association of anti–inflammatory treatments and Alzheimer's disease: Initial results of a co–twin control study. *Neurology* 44:227–232; 1994.

Busciglio, J. et al., Methodological variables in the assessment of beta amyloid neurotoxicity. *Neurobiol. Aging* 13:609–612; 1992.

Cai, X.D. et al., Release of excess amyloid β protein from a mutant amyloid β protein precursor. *Science* 259:514–516; 1993.

Cai, Z. et al., Amitriptyline, desipramine, cyproheptadine and carbamazepine, in concentrations used therapeutically, reduce kainate– and N–methyl–D–aspartate–induced intracellular $Ca^{2+}$ level in neuronal culture. *Eur. J. Pharmacol.* 219:53–57; 1992.

Callazo, D., Takahashi, H., and McKay, R.D.G., Cellular targets and trophic functions of neurotrophin–3 in the developing rat hippocampus. *Neuron* 9:643–656; 1992.

Cantiello, H.F., Stow, J.L., Prat, A.G., & Ausiello, D.A. Actin filaments regulate epithelial Na+ channel activity. *Am. J. Physiol.* 261, C882–888 (1991).

Capdevila, J., et al., Inhibitors of cytochrome P–450–dependent arachidonic acid metabolism. *Arch. Biochem. Biophys.* 261:257–263; 1988.

Chartier–Harlin, M.C. et al., Early–onset Alzheimer's disease caused by mutations at codon 717 of the β–amyloid precursor protein gene. *Nature* 353:844–846; 1991.

Cheng, B., and Mattson, M. P., IGF–I and IGF–II protect cultured hippocampal and septal neurons against calcium–mediated hypoglycemic damage. *J. Neurosci.* 12:1558–1566; 1992.

Cheng, B. et al., Glucose deprivation elicits neurofibrillary tangle–like antigenic changes in hippocampal neurons: Prevention by NGF and bFGF. *Exp. Neurol.* 117:114–123; 1992.

Cheng, B., Barger, S.W., and Mattson, M.P., Staurosporine, K–252a and K–252b stabilize calcium homeostasis and promote survival of CNS neurons in the absence of glucose. *J. Neurochem.* 1994, In press.

Choi, D.W., Ionic dependence of glutamate neurotoxicity. *J. Neurosci.* 7:369–379; 1987.

Citron, M. et al., Mutation of the β–amyloid precursor protein in familial Alzheimer's disease increases β–protein production. *Nature* 360:672–674; 1993.

Clemens, J.S. et al., LY178002 reduces rat brain damage after transient global forebrain ischemia. *Stroke* 22:1048–1052; 1991.

Copani, A. et al., β–amyloid increases neuronal susceptibility to injury by glucose deprovation. *NeuroReport* 2:763–675; 1991.

Drewes, G. et al., Mitogen activated protein (MAP) kinase transforms tau protein into an Alzheimer–like state. *EMBO J.* 11:2131–2138; 1992.

Dumuis, A. et al., NMDA receptors activate the arachidonic acid cascade system in striatal neurons. *Nature* 336:68–70; 1988.

Evans, J.F. et al., 5–lipoxygenase–activating protein is the target of a quinoline class of leukotriene synthesis inhibitors. *Mol. Pharmacol.* 40:22–27; 1991.

Goate, A. et al., Segregation of a missense mutation in the amyloid precursor protein gene with familial Alzheimer's disease. *Nature* 349:704–706; 1991.

Goodman, Y., and Mattson, M.P., Secreted forms of βAPP protect hippocampal neurons against Aβ–peptide–induced oxidative injury. *Exp. Neurol.* 128:1–12 (1994).

Greenamyre, J.T. et al., Excitatory amino acids and Alzheimer's disease. *Neurobiol. Aging* 10:593–602; 1989.

Grundke–Iqbal, I. et al., Abnormal phosphorylation of the microtubule–associated protein tau in Alzheimer cytoskeletal pathology. *Proc. Natl. Acad. Sci. U.S.A.* 83:4913–4917; 1986.

Grynkiewicz, G. et al., A new generation of $Ca^{2+}$ indicators with greatly improved fluorescence properties. *J. Biol. Chem.* 260:3440–3450; 1985.

Hall, E.D., Novel inhibitors of iron–dependent lipid peroxidation for neurodegenerative disorders. *Ann. Neurol.* 32:S137–S142; 1992.

Hartmann, H. et al., β–amyloid protein amplifies calcium signalling in central neurons from the adult mouse. *Biochem. Biophys. Res. Commun.* 194:1216–1220 (1993).

Henriksen, O., Johannessen S.I., Clinical and pharmacokinetic observations on sodium valproate: A 5–year follow–up study in 100 children with epilepsy. *Acta Neurol. Scandinav.* 65:504–523; 1982.

Hensley et al., A model for β–amyloid aggregation and neurotoxicity based on free radical generation by the peptide. *Proc. Natl. Acad. Sci. U.S.A.* 91:3270–3274 (1994).

Herbert, J. M., Seban, E., and Maffrand, J.P., Characterization of specific binding sites for [$^3$H]–staurosporine on various protein kinases. *Biochem. Biophys. Res. Commun.* 171:189–195; 1990.

Jesberger, J.A., and Richardson, J.S., Oxygen free radicals and brain dysfunction. *Int. J. Neurosci.* 57:1–17; 1991.

Johnson, B.D., & Byerly, L. A cytoskeletal mechanism for $Ca^{2+}$ channel metabolic dependence and inactivation by intracellular $Ca^{2+}$. *Neuron.* 10, 797–804 (1993).

Johnson. G.V.W. et al., Degradation of microtubule–associated protein 2 and brain spectrin by calpain: a comparative study. *J. Neurochem* 56:1630–1638; 1991.

Kane, D.J. et al., Bcl–2 inhibition of neural death: decreased generation of reactive oxygen species. *Science* 262:1274–1277; 1993.

Kennedy, M.B. Regulation of neuronal function by calcium. *Trends Neurosci.* 12, 417–420 (1989).

Knusel, B., and Hefti, F., Multiple and interactive responses of central neurons to neurotrophic factors. *Semin. Neurosci.* 5:259–267; 1993.

Koh, J.Y. et al., β–amyloid protein increases the vulnerability of cultured cortical neurons to excitotoxic damage. *Brain Res.* 533:315–320; 1990.

Lampe, H. et al., Carbamazepine blocks NMDA–activated currents in cultured spinal cord neurons. *Neuroreport* 1:26–28; 1990.

Lee, V.M. et al., A68: A major subunit of paired helical filaments and derivatized forms of normal tau. *Science* 251:675–678; 1991.

MacDonald, R.L. et al., Antiepileptic drug mechanisms of action. *Epilepsia* 34:S1–S8; 1993.

Mark, R.J. et al., Amyloid β–peptide impairs ion–motive ATPase activities: Evidence for a role in loss of neuronal $Ca^{2+}$ homeostasis and cell death. *J. Neurosci.* 15:6239–6249(1995).

Mattson, M.P., and Kater, S.B., Isolated hippocampal neurons in cryopreserved long–term cultures: Development of neuroarchitecture and sensitivity to NMDA. *Int. J. Dev. Neurosci.* 6:439–452; 1988.

Mattson, M.P. et al., Outgrowth regulating actions of glutamate in isolated hippocampal pyramidal neurons. *J. Neurosci.* 8:2087–2100; 1988.

Mattson M.P. et al., Roles for mitotic history in the generation and degeneration of hippocampal neuroarchitecture. *J. Neurosci.* 9:1223–1232; 1989.

Mattson, J.P. et al., Excitatory and inhibitory neurotransmitters in the generation and degeneration of hippocampal neuroarchitecture. *Brain Res.* 478:337–348; 1989.

Mattson, M.P., Antigenic changes similar to those seen in neurofibrillary tangles are elicited by glutamate and calcium influx in cultured hippocampal neurons. *Neuron* 4:105–117; 1990.

Mattson, M.P. et al., Effects of elevated intracellular calcium levels on the cytoskeleton and tau in cultured human cortical neurons. *Mol. Chem. Neuropathol.* 15:117–142; 1991.

Mattson, M.P., Effects of microtubule stabilization and destabilization on tau immunoreactivity in cultured hippocampal neurons. *Brain Res.* 582:107–118; 1992.

Mattson et al., Fibroblast growth factor and glutamate: opposing roles in the generation and degeneration of hippocampal neuroarchitecture. *J. Neurosci.* 9:3728–3740; 1989.

Mattson, M.P., Calcium as sculptor and destroyer of neural circuitry. *Exp. Gerontol.* 27:29–49; 1992.

Mattson, M.P. et al., β–amyloid peptides destabilize calcium homeostasis and render human cortical neurons vulnerable to excitotoxicity. *J. Neurosci.* 12:379–389; 1992.

Mattson, M.P., Cheng, B., and Smith–Swintosky, V.L., Neurotrophic factor mediated protection from excitotoxicity and disturbances in calcium and free radical metabolism. *Seminars Neurosci.* 5:295–307, 1993.

Mattson, M.P. et al., Calcium–destabilizing and neurodegenerative effects of aggregated β–amyloid peptide are attenuated by basic FGF. *Brain Res.* 621:35–49; 1993.

Mattson, M.P. et al., β–Amyloid precursor protein metabolites and loss of neuronal calcium homeostasis in Alzheimer's disease. *Trends Neurosci.* 16:409–415; 1993.

Mattson, M.P. et al., Calcium, free radicals, and excitotoxic neuronal death in primary cell culture. *Meth. Cell Biol.* 46:187–216 (1995).

Matus, A. Microtubule–associated proteins: Their potential role in determining neuronal morphology. *Annu. Rev. Neurosci.* 11, 29–44 (1988).

McDonald, J.W. et al., Pharmacology of N–methyl–D–aspartate–induced brain injury in an in vivo perinatal rat model. *Synapse* 6:179–188; 1990.

Mehler, et al., Enhanced sensitivity of hippocampal pyramidal neurons from mdx mice to hypoxia–induced loss of synaptic transmission. *Proc. Natl. Acad. Sci. U.S.A.* 89:2461–2465; 1992.

Monyer, H. et al., 21–Aminosteroids attenuate excitotoxic neuronal injury to cortical cell cultures. *Neuron* 5:121–126; 1990.

Mori, H. et al., Ubiquitin is a component of paired helical filaments in Alzheimer's disease. *Science* 235:1641–1644; 1987.

Mullan, M. et al., Genetic and molecular advances in Alzheimer's disease. *Trends Neurosci.* 16:398–403; 1993.

Murrell, J. et al., A mutation in the amyloid precursor protein associated with hereditary Alzheimer's disease. *Science* 254:97–99; 1991.

Nakanishi, S., Matsuda, Y., Iwahashi, K., and Kase, H., K–252b, c and d, potent inhibitors of protein kinase C from microbial origin. *J. Antibiot.* (Tokyo) 39:1066–1071; 1986.

Nilsson, M. et al., Agonist–evoked $Ca^{2+}$ transients in primary astroglial cultures—modulatory effects of valproic acid. *Glia* 5:201–209; 1992.

Page, B. et al., A new fluorometric assay for cytotoxicity measurements in vitro. *Int. J. Oncology* 3:473–476; 1993.

Pike, C.J. et al., In vitro aging of β–amyloid protein causes peptide aggregation and neurotoxicity. *Brain Res.* 563:311–314; 1991.

Pike, C.J. et al., Neurodegeneration induced by β–amyloid peptides in vitro; the role of peptide assembly state. *J. Neurosci.* 13:1676–1687; 1993.

Rogers, J. et al., Clinical trial of indomethacin in Alzheimer's disease. *Neurology* 43:1609–1611; 1993.

Ponchaut, S. et al., In vitro effects of valproate and valproate metabolites on mitochondrial oxidations. Relevance of CoA sequestration to the observed inhibitions. *Biochem. Pharmacol.* 43:2435–2442; 1992.

Potter, P.E. et al., Dephenylhydantoin attenuates hypoxia–induced release of $^3H$–glutamate from rat hippocampal slices. *Brain Res.* 558:127–130; 1991.

Rosenkranz, A.R. et al., A microplate assay for the detection of oxidative products using 2',7'–dichlorofluorescin–diacetate. *J. Immunol. Methods* 156:39–45; 1992.

Rosenmund, C., & Westbrook, Calcium–induced actin depolymerization reduces NMDA channel activity. G.L. *Neuron.* 10, 805–814 (1993).

Rothman, S.M. et al., Nordihydroguaiaretic acid attenuates NMDA neurotoxicity–action beyond the receptor. *Neuropharmacol.* 32:1279–1288; 1993.

Sautiere P.E. et al., Tau antigenic changes induced by glutamate in rat primary culture model: a biochemical approach. *Neurosci. Lett.* 140:206–210; 1992.

Schubert, D. et al., Growth factors and vitamin E modify neuronal glutamate toxicity. *Proc. Natl. Acad. Sci. USA* 89:8264–8267; 1992.

Selkoe, D.J., The molecular pathology of Alzheimer's disease. *Neuron* 6:487–498; 1991.

Selkoe, D.J., Physiological production of the β–amyloid protein and the mechanism of Alzheimer's disease. *Trends Neurosci.* 16:403–409; 1993.

Seubert, P. et al., Isolation and quantitation of soluble Alzheimer's β–peptide from biological fluids. *Nature* 359:325–327; 1992.

Seubert, P. et al., Secretion of β–amyloid precursor protein cleaved at the amino terminus of the β–amyloid peptide. *Nature* 361:260–263; 1993.

Sgaragli, G.P., et al. (1993) Calcium antagonist and antiperoxidant properties of some hindered phenols. *Br. J. Pharmacol.* 110, 369–377.

Siman, R. et al., Excitatory amino acids activate calpain I and induce structural protein breakdown in vivo. *Neuron* 1:279–287; 1988.

Steppuhn, K.G. et al., Modulation of the seizure threshold for excitatory amino acids in mice by antiepileptic drugs and chemoconvulsants. *J. Pharmacol. Exp. Ther.* 265:1063–1070; 1993.

Taft, W.C. et al., Phenytoin protects against ischemia–produced neuronal cell death. *Brain Res.* 483:143–148; 1989.

Tischler, A.S., Ruzicka, L.A., and Hobner, P.R., A protein kinase inhibitor, staurosporine, mimics nerve growth factor induction of neurotensin/neuromedia N gene expression. *J. Biol. Chem.* 266:1141–1146; 1991.

Ueda, K. et al., Alz–50 recognizes a phosphorylated epitope of Tau protein. *J. Neurosci.* 10:3295–3304; 1990.

Verity, M.A., Mechanisms of phospholipase $A_2$ activation and neuronal injury. *Ann. N.Y. Acad. Sci.* 679:110–120; 1993.

Wallis, R.A. et al., Protection from hypoxic and N–methyl–D–aspartate injury with azelastine, a leukotriene inhibitor. *Eur. J. Pharmacol.* 238:165–171; 1993.

Yanker, B.A. et al., Neurotrophic and neurotoxic effects of amyloid β protein: reversal by tachykinin neuropeptides. *Science* 250:279–282; 1990.

Yoshimoto, T. et al., 2,3,5–trimethyl–6–(12–hydroxy–5, 10–dodecadiynyl)–1,4–benzoquinone (AA861), a selective inhibitor of the 5–lipoxygenase reaction and the biosynthesis of slow–reacting substance of anaphylazis. *Biochim. Biophys. Acta* 713:470–473; 1982.

Zeise, M.L. et al., Valproate suppresses N–methyl–D–aspartate–evoked, transient depolarizations in the rat neocortex in vitro. *Brain Res.* 544:345–348; 1991.

Zhang, Y. et al., Basic FGF, NGF, and IGFs protect hippocampal and cortical neurons against iron–induced degeneration. *J. Cerebral. Blood Flow Metab.* 13:378–388; 1993.

Furukawa et al, Journal of Neurochemistry, vol. 65, No. 3, Sep. 1995, pp. 1061–1068.

CYTOCHALASINS USEFUL IN PROVIDING PROTECTION AGAINST NERVE CELL INJURY ASSOCIATED WITH NEURODEGENERATIVE DISORDERS

FIELD OF THE INVENTION

The present invention relates to a novel therapeutic use of certain compounds to protect nerve cells from injury and death. The compounds include cytochalasin D and related analogs, and cytochalasin E and related analogs.

BACKGROUND OF THE INVENTION

Nerve cell injury and death leads to a number of. neurodegenerative disorders such as Alzheimer's disease and stroke.

The leading cause of dementia and the fourth leading cause of death in the developed world is Alzheimer's disease which afflicts an estimated 10% of the population over 65 years of age in the United States. Alzheimer's disease imposes a tremendous financial burden on afflicted individuals because they require prolonged care.

Affected individuals are at first forgetful. As this progressive disorder gradually worsens, these affected individuals, although able to recall occurrences in the distant past, are unable to remember recent events. Subsequently, speech, the ability to calculate, visuospatial orientation, judgement, and social behavior become progressively abnormal. Eventually, profound dementia sets in and frequently the individual dies of superimposed infections. The duration of diseases ranges from 3 to 10 years.

The diagnosis of Alzheimer's disease is usually made on the basis of clinical history, neurological examination and laboratory tests that help to exclude other disorders, some of which are potentially treatable. Unfortunately, other than direct examination of brain tissue obtained by cerebral biopsy or at autopsy, no tests to establish a diagnosis of Alzheimer's disease presently exist.

At autopsy, the brains of individuals with Alzheimer's disease are usually slightly smaller than normal for their age. Microscopic examination discloses four characteristic pathological features that are essential for the diagnosis of Alzheimer's disease: neurofibrillary tangles, loss of specific population of nerve cells, senile plaques and deposits of amyloid.

Neurofibrillary tangles, that is, fibrillar inclusions within cell bodies of affected neurons, consist of abnormal filaments thought to be derived in part from cytoskeletal elements normally present in nerve cells. Neurofibrillary tangles consist of abnormal accumulations of cytoskeletal and other proteins whereas senile plaques consist of aggregates of amyloid β-peptide (Aβ). Major components of neurofibrillary tangles are the microtubule-associated protein tau, and ubiquitin, a "heat-shock" protein involved in targeting proteins for proteolytic degradation. Postranslational alterations in tau such as phosphorylation, and disassociation of tau from microtubules may promote the assembly of tau into the abnormal straight and paired helical filaments that characterize neurofibrillary tangles. Although the mechanism leading to neurofibrillary degeneration is not clear, several observations suggest a role for dysregulation of neuronal calcium homeostasis with resultant elevations of intracellular free calcium concentration, $[Ca^{2+}]_i$. Among the evidence supporting this hypothesis is: experimentally induced elevations of $[Ca^{2+}]_i$ in hippocampal neurons (in vitro and in vivo) can elicit antigenic, biochemical and ultrastructural changes in cytoskeletal proteins (tau and spectrin) similar to those seen in neurofibrillary tangles; neurons vulnerable to neurofibrillary degeneration bear high levels of glutamate receptors; aggregated Aβ can be neurotoxic and can render neurons vulnerable to excitotoxicity by a mechanism that involves destabilization of $[Ca^{2+}]_i$ homeostasis. In addition, studies indicate that mitogen-activated protein (MAP) kinases can phosphorylate tau in a manner very similar to that observed in the paired helical filaments of Alzheimer's disease, and MAP kinases are known to be activated glutamate and elevation of $[Ca^{2+}]_i$.

Degeneration and death of certain populations of nerve cells occur in certain brainstem nuclei, the basal forebrain, the amygdala, the hippocampus and neocortex. In the brain, specific populations of nerve cells use specific neurotransmitters. Also, neurochemical studies have shown that the brains of individuals with Alzheimer's disease exhibit a selective reduction in markers for certain neurotransmitter systems.

The third characteristic brain abnormality associated with Alzheimer's disease is the presence of abundant senile plaques, composed of several elements: abnormal neurites (enlarged filament-containing axons and terminals), extracellular amyloid fibrils and non-neuronal reactive cells. The presence of plaques correlates with the presence of dementia and with the severity of loss of certain neurotransmitter markers, particularly cholinergic enzymes.

Localized in plaques and around cerebral blood vessels, amyloid is composed of a 4-kilodalton protein designated amyloid β-peptide. The amyloid β-peptide is a 40–42 amino acid peptide arising from a much larger membrane-spanning β-amyloid precursor protein (695–770 amino acids) which is a transmembrane glycoprotein that accumulates as diffuse (unaggregated) and compact (aggregated) plaques in the brain of victims of Alzheimer's disease. The diffuse plaques are not associated with neuronal pathology, whereas compact Aβ is surrounded by degenerative neurites with characteristic cytoskeletal pathology. Cell culture studies have shown that Aβ can be directly neurotoxic, and can render neurons vulnerable to excitotoxicity and oxidative injury. The mechanism of Aβ toxicity is related to its secondary structure and appears to involve free radical-mediated damage to the plasma membrane and disruption of cellular calcium homeostasis resulting in elevated rest $[Ca^{2+}]_i$ and increased $[Ca^{2+}]_i$ responses to depolarization and excitatory amino acids.

The major pathway for β-amyloid precursor protein (βAPP) metabolism involves an enzymatic cleavage within the Aβ sequence and obviates deposition of amyloidogenic Aβ. On the other hand, Aβ is released from brain cells at low levels and is present in the cerebrospinal fluid at nanomolar concentrations indicating an alternative processing pathway of βAPP. A cleavage of βAPP at the N-terminus of Aβ leaves behind a C-terminal fragment of βAPP which contains potentially amyloidogenic Aβ. Some cases of inherited Alzheimer's disease have been linked to mutations in βAPP which may alter processing of βAPP in a way that leads to increased production of AS. The link between altered metabolism of βAPP and neuronal injury in Alzheimer's disease is supported by studies showing that synthetic Aβ peptides can be directly neurotoxic to primary cultures of hippocampal and cortical neurons, and can render neurons vulnerable to glutamate excitotoxicity, glucose deprivation, and oxidative injury. The neurotoxicity of Aβ is dependent upon its ability to form aggregates which accumulate at plasma membranes and disrupt cellular calcium homeostasis. The mechanism whereby Aβ disrupts calcium regulation at the plasma membrane may involve the peptide forming calcium-conducting pores.

Calcium influx through glutamate receptors and voltage dependent channels mediates an array of functional and structural responses in neurons. However, unrestrained calcium influx can injure and kill neurons; such calcium overload can be induced by the excitatory transmitter glutamate and Alzheimer amyloid β-peptide, and is therefore implicated in both acute and chronic neurodegenerative conditions. Actin microfilaments are a major cytoskeletal element whose polymerization state is highly sensitive to calcium. Several key adaptive physiological processes in the brain, including neurotransmitter release, postsynaptic signalling and regulation of neurite outgrowth and synaptogenesis during development are triggered by calcium influx. However, excessive calcium influx plays a primary role in excitotoxicity, a form of neuronal injury resulting from overstimulation of glutamate receptors, and which is believed operative in a variety of both acute (e.g., stroke and traumatic brain injury) and chronic (e.g., Alzheimer's and Huntington's diseases) neurodegenrative conditions. In Alzheimer's disease the 40–42 amino acid amyloid β-peptide which forms insoluble plaques in the brain may kill neurons by inducing $Ca^{2+}$ influx and increasing sensitivity to excitotoxicity.

Actin and tubulin are two major structural proteins in neurons which polymerize to form microfilaments and microtubules, respectively. Microfilaments and microtubules are highly dynamic structures exquisitely sensitive to environmental stimuli that elevate $[Ca^{2+}]_i$, such as glutamate.

Stroke is our nation's third leading killer and the number one cause of adult disability. One-half million people suffer a stroke each year. A stroke is the result of a sudden decrease in the flow of blood to an area of the brain. When blood cannot reach the brain, brain cells become deprived of oxygen and die. Consequently, functions normally controlled by the damaged brain area become impaired. For example, paralysis of certain body parts may occur. The interruption in blood flow can be due to blockage from a blood clot or narrowed artery in the head or neck or to the bursting of an artery in the brain.

Nerve cell injury and death is also responsible for other neurodegenerative disorders such as Down's syndrome, amyotrophic lateral sclerosis, Parkinson's disease, Huntington's disease, Cerebral ischemia, cerebral infarction, cerebral vasospasm, hypoglycemia, cardiac arrest, status epilepticus, perinatal asphyxia, anoxia, pulmonary surgery, or cerebral trauma.

SUMMARY OF THE INVENTION

The present invention relates to a novel therapeutic use of certain compounds to protect nerve cells from injury and death. The compounds include cytochalasin D and related analogs, and cytochalasin E and related analogs. More particularly, the present invention concerns a method for reducing adverse effects of a neurodegenerative disorder comprising: administering to a patient a therapeutically effective amount of at least one compound selected from the group consisting of compounds represented by Formulas (I)–(II) and their pharmaceutically acceptable salts:

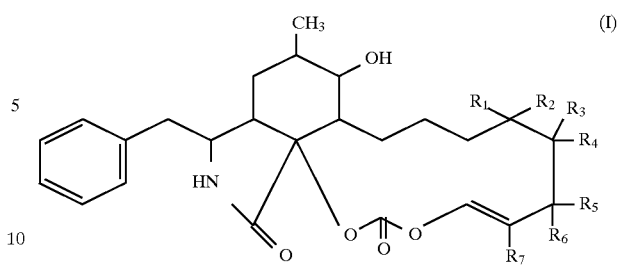

where $R_1$, $R_2$, $R_3$, $R_4$, $R_5$, $R_6$, and $R_7$ represent hydrogen, $C_1$ to $C_6$ alkyl or hydroxy, or where $R_3$ and $R_4$ together represent a carbonyl group; or

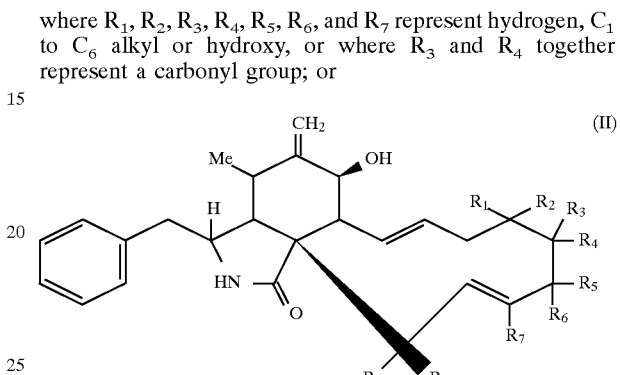

where $R_1$, $R_2$, $R_3$, $R_4$, $R_5$, $R_6$, $R_7$, $R_8$, and $R_9$ represent hydrogen, $C_1$ to $C_6$ alkyl, hydroxy, or OAC, or where $R_3$ and $R_4$ together represent a carbonyl group.

The present invention also relates to a pharmaceutical composition comprising at least one compound selected from the group consisting of compounds represented by Formulas (I)–(II) and their pharmaceutically acceptable salts:

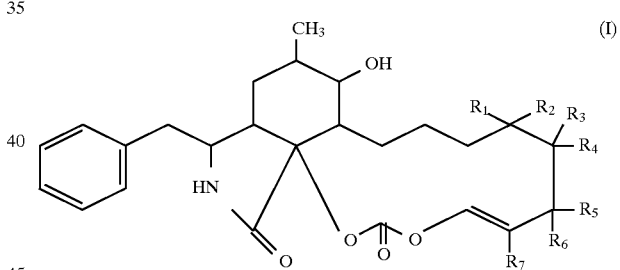

where $R_1$, $R_2$, $R_3$, $R_4$, $R_5$, and $R_7$ represent hydrogen, $C_1$ to $C_6$ alkyl or hydroxy, or where $R_3$ and $R_4$ together represent a carbonyl group; or

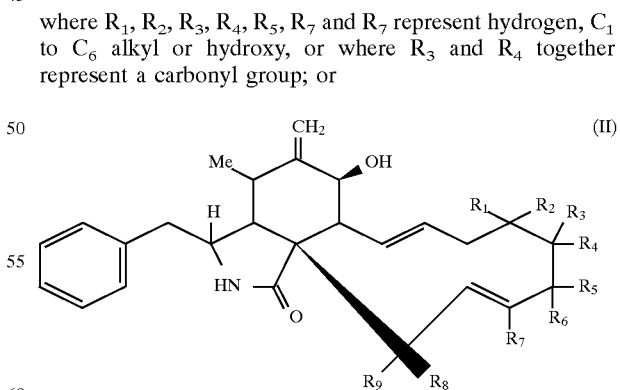

where $R_1$, $R_2$, $R_3$, $R_4$, $R_5$, $R_6$, $R_7$, $R_8$, and $R_9$ represent hydrogen, $C_1$ to $C_6$ alkyl, hydroxy, or OAC, or where $R_3$ and $R_4$ together represent a carbonyl group.

Neurodegenerative disorders treatable by the present method include, but are not limited to, Alzheimer's disease, Down's syndrome, amyotrophic lateral sclerosis, Parkinson's disease, Huntington's disease, cerebral ischemia, cerebral infarction, thromboembolic and hemorrhagic stroke, cerebral vasospasm, hypoglycemia, cardiac arrest, status epilepticus, perinatal asphyxia, anoxia, pulmonary surgery, or cerebral trauma.

The present invention also relates to a method of attenuating intracellular calcium levels in mammalian nerve cells of a patient in need of therapy for amyloid-β peptide toxicity associated with neurodegenerative disorders which comprises administration to a mammal in need of such therapy an effective amount of a compound which attenuates intracellular calcium levels in the mammalian nerve cell.

Other features of the invention will become apparent in the course of the following description of the exemplary embodiments which are given for illustration of the invention and are not intended to be limiting thereof.

DETAILED DESCRIPTION OF THE INVENTION

Figure 1A:
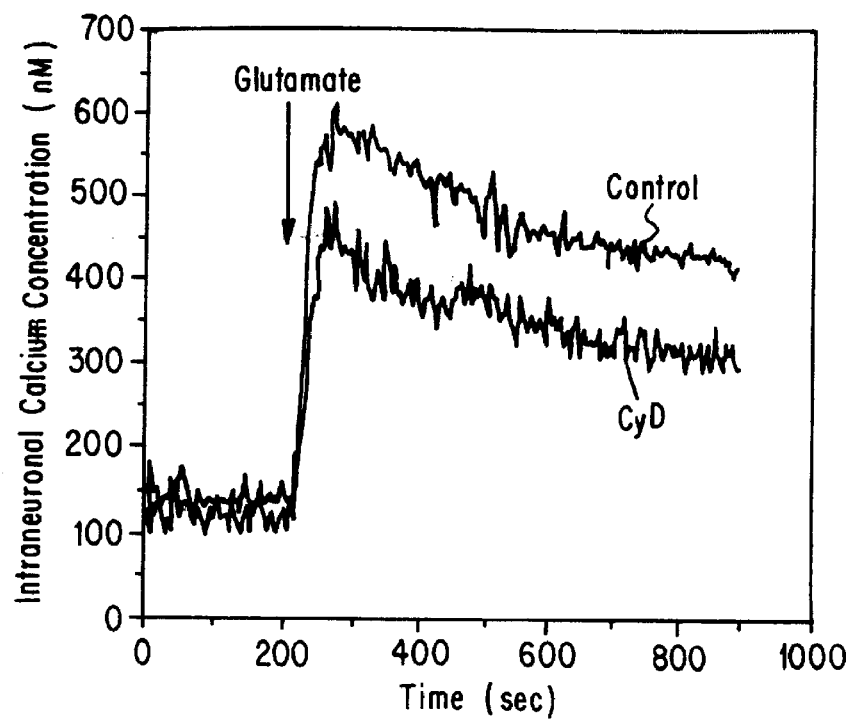
FIGS. 1A, 1B, 1C and 1D show that cytochalasin D attenuates $[Ca^{2+}]_i$ responses to glutamate, Aβ and membrane depolarization.
Figure 1B:
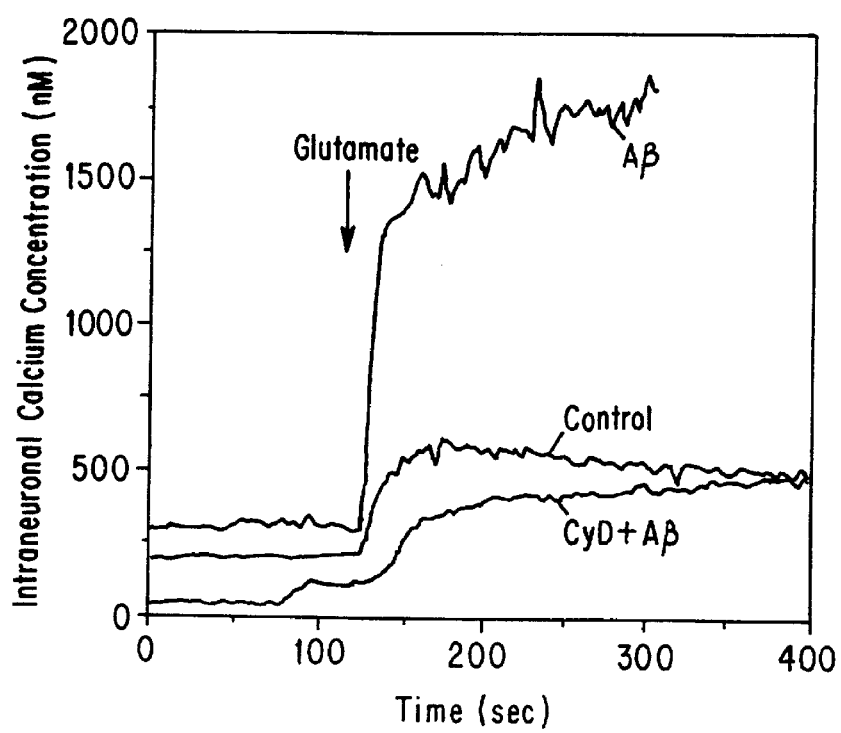
Figure 1C:
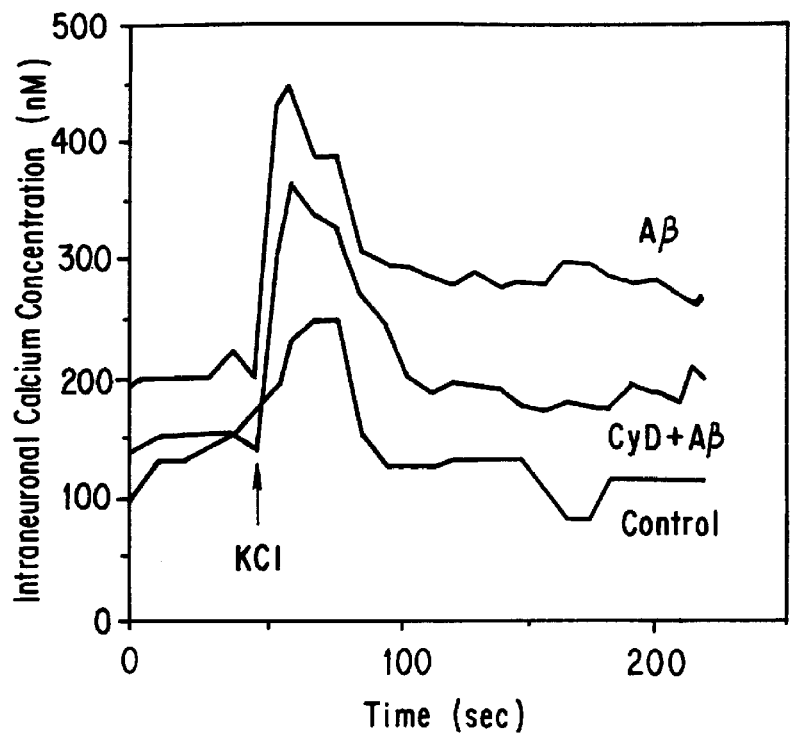
Figure 1D:
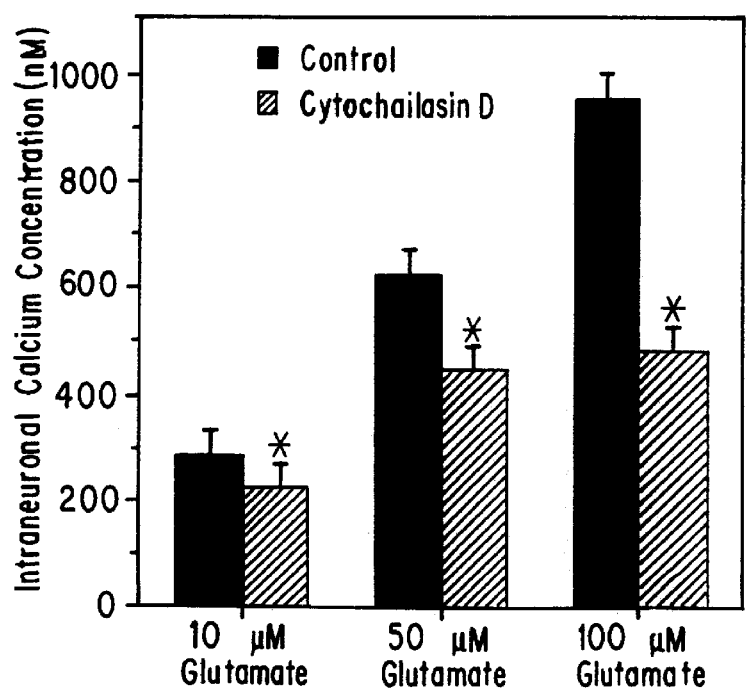
Figure 2A:
FIGS. 2A–2D show cresyl violet-stained coronal sections from brains of rats administered kainate alone or kainate plus cytochalasin D.
Figure 2B:
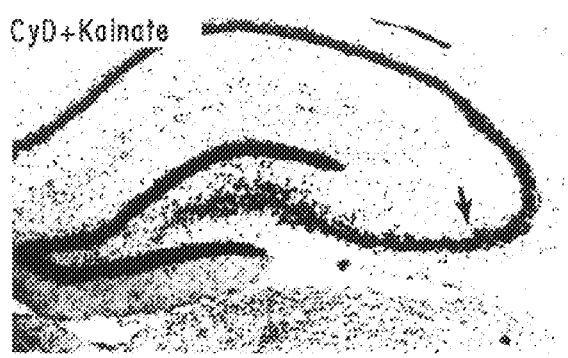
Figure 2C:
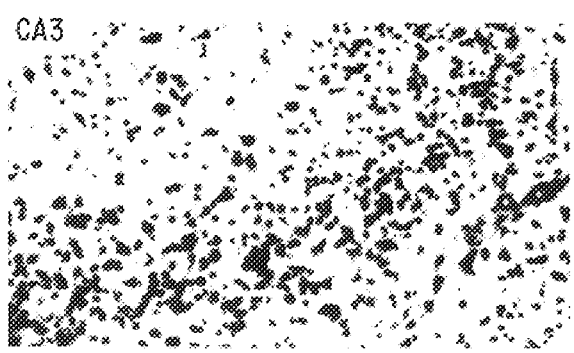
Figure 2D:

The present invention is based, in part, on the inventors' surprising and unexpected discovery of a method for reducing adverse effects of a neurodegenerative disorder comprising: administering to a patient a therapeutically effective amount of at least one compound selected from the group consisting of compounds represented by Formulas (I)–(II) and their pharmaceutically acceptable salts:

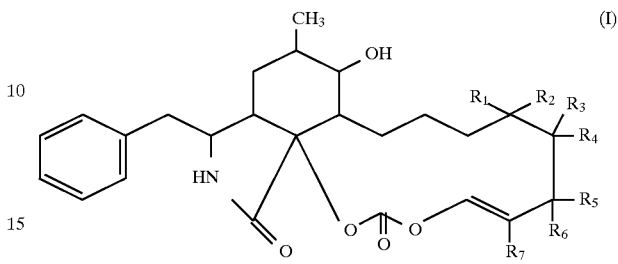

where $R_1$, $R_2$, $R_3$, $R_4$, $R_5$, $R_6$, and $R_7$ represent hydrogen, $C_1$ to $C_6$ alkyl or hydroxy, or where $R_3$ and $R_4$ together represent a carbonyl group; or

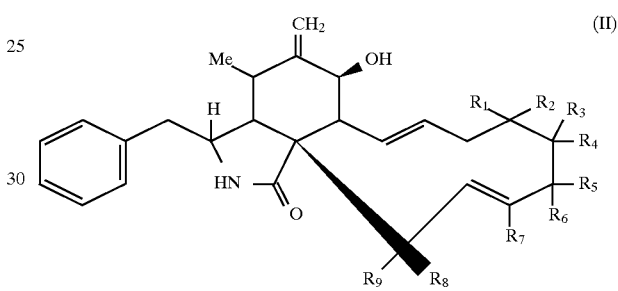

where $R_1$, $R_2$, $R_3$, $R_4$, $R_5$, $R_6$, $R_7$, $R_8$, and $R_9$ represent hydrogen, $C_1$ to $C_6$ alkyl, hydroxy, or OAC, or where $R_3$ and $R_4$ together represent a carbonyl group.

The present invention is also based, in part, on the inventors' surprising and unexpected discovery of a method of attenuating intracellular calcium levels in mammalian nerve cells of a patient in need of therapy for amyloid-β peptide toxicity associated with neurodegenerative disorders which comprises administration to a mammal in need of such therapy an effective amount of a compound which attenuates intracellular calcium levels in the mammalian nerve cell.

Neurodegenerative disorders treatable by the present method include, but are not limited to, Alzheimer's disease, Down's syndrome, amyotrophic lateral sclerosis, Parkinson's disease, Huntington's disease, cerebral ischemia, cerebral infarction, thromboembolic and hemorrhagic stroke, cerebral vasospasm, hypoglycemia, cardiac arrest, status epilepticus, perinatal asphyxia, anoxia, pulmonary surgery, or cerebral trauma.

A preferred compound represented by Formula (I) is cytochalasin D and is sold commercially by Sigma Chemical Company under that name. Cytochalasin D has the following structural formula:

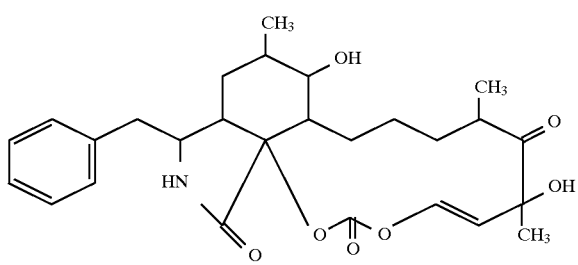

A preferred compound represented by Formula (II) is cytochalasin E and is sold commercially by Sigma Chemical Company under that name. Cytochalasin E has the following structural formula:

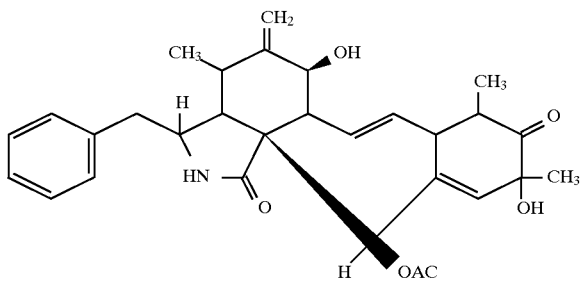

The compounds for use in the present invention can be administered as a pharmaceutical composition. The pharmaceutical compositions used in the methods of this invention for administration to animals and humans comprise an active agent in combination with a pharmaceutical carrier or excipient acceptable for delivery of the compounds to neurons.

The pharmaceutical compositions can be in the form of tablets (including lozenges and granules), dragees, capsules, pills, ampoules or suppositories comprising a compound of the invention. "Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the composition contains a daily dose, or for example, a half, a third or a quarter of a daily dose will depend on whether the pharmaceutical composition is to be administered once or, for example, twice, three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian.

The active agents can also be administered as suspensions, solutions and emulsions of the active compound in aqueous or non-aqueous diluents, syrups, granulates or powders. Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active agent can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid) or mixtures of these diluents.

The pharmaceutical compositions which are solutions and emulsions can, for example, contain the customary diluents (with, of course, the above-mentioned exclusion of solvents having a molecular weight below 200, in the presence of a surface-active agent), such as diluents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), polycrystalline cellulose, aluminum methahydroxide, agar-agar and tragacanth, or mixtures thereof.

The pharmaceutical compositions can also contain bulking agents and preservatives, as well as perfumes and flavoring additions (e.g., peppermint oil and eucalyptus oil, and sweetening agents, (e.g., saccharin and aspartame).

The pharmaceutical compositions will generally contain from about 0.0001 to 90 wt. %, preferably about 0.01 to 10 wt. % of the active ingredient by weight of the total composition. In addition to the active agent, the pharmaceutical compositions and medicaments can also contain other pharmaceutically active compounds.

Any diluent in the pharmaceutical compositions of the present invention may be any of those mentioned above in relation to the pharmaceutical compositions. Such compositions may include solvents of molecular weight less than 200 as the sole diluent.

The active compound is administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.0001 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

EXAMPLE 1

(hippocampal cell culture and experimental treatments)

Dissociated embryonic rat hippocampal cell cultures were established and maintained. All procedures conformed with the NIH *Guide for the Care and Use of Laboratory Animals* and were approved by the University of Kentucky Animal Care and Use Committee. Cultures were maintained on a polyethyleneimine-coated substrate in plastic 35-mm dishes or 96 wall plates (for cell survival studies) or glass-bottom 35-mm dishes (for $[Ca^{2+}]_i$ imaging studies). The cell density was ~70–100 cells/mm$^2$. Cells were maintained in Eagle's minimum essential medium supplemented 10% with fetal bovine serum and containing 20 mM sodium pyruvate. All experiments were performed in 6–10-day-old cultures, a time at which neurons exhibit calcium responses to glutamate mediated by both NMDA and α-amino-3-hydroxy-5-methylisoxazole-4-propionic acid (AMPA)/kainate receptors, and are vulnerable to excitotoxicity and Aβ toxicity. Aβ25–35 (Bachem, lot ZJ744) and Aβ1–40 (Bachem, lot ZK600) were stored in the lyophilized form, and stocks were prepared immediately before use by dissolving the peptide at a concentration of 1 mM in sterile distilled water. Preliminary characterization of the aggregation kinetics and neurotoxicity profiles of each of these peptides showed that the peptides aggregated rapidly when placed in culture medium and progressively killed neurons over a 48-h period when added to cultures in a soluble form. Glutamate and colchicine (Sigma) were prepared as 200–500x stocks in saline. Cytochalasins D and E (Sigma) and calcium ionophore 4-bromo-A23187 (Calbiochem) were prepared as 500x stocks in dimethyl sulfoxide. Vitamin E (α-tocopherol; Sigma) was prepared as a 500x stock in ethanol. Nordihydroguaiaretic acid and $FeSo_4$ were prepared as 500x stocks in sterile water.

EXAMPLE 2

(analysis of neuronal survival)

Neuronal survival was quantified by counting viable neurons in the same microscope fields (10x objective) immediately before experimental treatment and at time points after treatment. In addition, cells were grown in 96-well plates and Alamar blue fluorescence (Alamar Laboratories) was quantified by using a fluorescence plate reader. Alamar Blue is a non-fluorescent substrate that, after reduction by cell metabolites, becomes fluorescent. Usually neurons that died in the time intervals (20–48 h) between examination points were absent. Viability of the remaining neurons was assessed by morphological criteria. Neutrons with intact neurites of uniform diameter and a soma with a smooth, round appearance were considered viable, whereas neurons with fragmented neurites and a vacuolated or swollen soma were considered nonviable. Survival values were expressed as percentages of the initial number of neurons present before experimental treatment. Statistical comparisons were made using ANOVA and Scheffe post-hoc tests for pairwise comparisons.

TABLE 1

Effects of cytochalasin D and colchicine on neurotoxicity of glutamate and Aβ

| Treatment Condition<br>Alamar Blue Assay | Neuron Survival (% of control)<br>Cell Counts |
|---|---|
| Vehicle (DMSO) | 100 ± 2.4 |
| 100 ± 3.6 | |
| 10 nM Cytochalasin D | 97 ± 7.8 |
| 89 ± 2.4 | |
| 100 nM Cytochalasin D | 91 ± 5.9 |
| 87 ± 2.2 | |
| 100 nM Colchicine | 40 ± 5.2[b] |
| 85 ± 1.9[a] | |
| 100 μM Glutamate | 18 ± 5.4[b] |
| 15 ± 3.3[b] | |
| 100 μM Glutamate + 10 nM CYD | 43 ± 6.7[d] |
| 54 ± 7.4[c] | |
| 100 μM Glutamate + 100 nM CYD | 42 ± 4.2[d] |
| 45 ± 9.8[d] | |
| 100 μM Glutamate + 100 nM Colch | 12 ± 2.2[b] |
| 24 ± 7.4 | |
| 50 μM Aβ | 47 ± 3.5[b] |
| n.d. | |
| 50 μM Aβ + 10 nM Cytochalasin D | 55 ± 2.5 |
| n.d. | |
| 50 μM Aβ + 100 nM Cytochalasin D | 74 ± 1.3[e] |
| n.d. | |
| 50 μM Aβ + 100 nM Colchicine | 23 ± 2.8 |
| n.d. | |
| 20 μM Glutamate | 74 ± 0.7[b] |
| n.d. | |
| 50 μM Aβ + 20 μM Glutamate | 24 ± 0.8[f] |
| n.d. | |
| 50 μM Aβ + 20 μM Glut ± | 63 ± 2.5[g] |
| n.d. | |
| 100 nM CyD | |

Values represent the means and SEM of 4 separate cultures (cell counts) or 4 culture wells (Alamar blue assay). [a]$p<0.05$ compared to control value. [b]$p<0.001$ compound to control value. [c]$p<0.01$ compared to value for glutamate-treated cultures. [d]$p<0.005$ compared to value for glutamate-treated cultures. [e]$p<0.001$ compared to value for Aβ-treated cultures. [f]$p<0.001$ compared to value for cultures treated with 20 μM glutamate. [g]$p<0.001$ compared to cultures treated with 50 μM Aβ+20 μM glutamate. n.d. not determined.

At concentrations known to depolymerize actin, cytochalasin D alone (1–100 nM) had no significant effect on neuronal survival, while colchicine (100 nM) reduced survival (Table 1). Although cytochalasin D did not adversely affect neuronal survival, it did inhibit growth cone motility. Neuronal survival in cultures exposed to 100 μM glutamate for 24 hr was reduced to less than 20%. Glutamate neurotoxicity was significantly attenuated in cultures pretreated for 1 hr with cytochalasin D, whereas colchicine was ineffective (Table 1). Neuronal survival was reduced in less than 50% of control values in cultures exposed for 24 hr to 50 μM Aβ25–35 (Table 1). Aβ neurotoxicity was essentially eliminated in parallel culture cotreated with 100 nM cytochalasin D, whereas colchicine exacerbated Aβ toxicity (Table 1). Cytochalasin E(10–100 nM), another microfilament-disrupting agent, also protected cultural hippocampal neurons against the toxicities of glutamate and Aβ.

EXAMPLE 3

(measurement of $[Ca^{2+}]_i$

Fluorescence ratio imaging of the $Ca^{2+}$ indicator dye fura-2 was used to quantify $[Ca^{2+}]_i$ in neuronal somata. Cells were incubated for 30–40 min in the presence of 2 μM acetoxymethyl ester form of the $[Ca^{2+}]_i$ indicator dye fura-2 and were then washed twice (2 ml/wash) with fresh medium and allowed to incubate at least 40 min before imaging. Immediately before imaging, the normal culture medium was replaced with Hanks' balanced saline solution (GIBCO) containing 10 mM HEPES buffer and 10 mM of glucose. Cells were imaged using a Zeiss Attofluor system with a oil objective or Quantex system with a 40x oil objective. The ratio of the fluorescence emission using two different excitation wavelengths (334 and 380 nm) was used to determine $[Ca^{2+}]_i$. The system was calibrated using solutions containing either no $Ca^{2+}$ or a saturating level of $Ca^{2+}$ (1 mM) according to the following formula: $[Ca^{2+}]_i = K_D[(R-R_{min})/(R_{max}-R)] (F_0/F_s)$. Values represent the average $[Ca^{2+}]_i$ in the neuronal cell body. Experimental treatments were added to the bathing medium by dilution from 100–500x stocks.

EXAMPLE 4

(localization of phalloidin with fluorescence microscopy

Hippocampal cells were exposed to cytochalasin D and then fixed for 30 min in 4% paraformaldehyde/phosphate-buffered saline. Cell membranes were permeabilized by incubating for 5 min in a solution of 0.2% Triton X-100 in phosphate-buffered saline. Cells were then incubated for 30 min in PBS containing 0.005 U/ml fluorescein-phalloidin (Molecular Probes). Cells were rinsed in water and mounted in Vectashield antifade solution (Vector Laboratories). Fluorescence images were acquired using a Sarastro 2000 confocal laser scanning microscope with a 60x oil-immersion objective. All images were acquired using identical settings for excitation intensity and detector gain.

EXAMPLE 5

Fura-2 calcium imaging technology revealed that cytochalasin D attenuated $[Ca^{2+}]_i$ responses to glutamate, Aβ, and membrane depolarization (FIG. 1). In control cultures, 50 μM glutamate induced a rapid approximately five-fold increase in neuronal $[Ca^{2+}]_i$. In contrast, the $[Ca^{2+}]_i$ response to glutamate in neurons pretreated with 100 nM cytochalasin D for 1 hr was reduced by approximately 30% (FIG. 1A). The neuronal $[Ca^{2+}]_i$ response to glutamate was greatly enhanced in cultures pretreated with Aβ for 3 hr; $[Ca^{2+}]_i$ rapidly rose to well over 1 μM compared to an increase to approximately 600 nM in neurons in untreated control cultures. Cytochalasin D completely blocked potentiation of $[Ca^{2+}]_i$ response to glutamate in Aβ-pretreated culture (FIG. 1B). Cytochalasin D pretreatment also suppressed $K^+$-induced elevation of $[Ca^{2+}]_i$ (FIG. 1C). Colchicine alone caused an elevation of rest $[Ca^{2+}]_i$ and did not attenuate $[Ca^{2+}]_i$ response to glutamate or Aβ (data not shown). Taken together with the previous patch clamp studies of Rosenmund and Westbrook and Johnson and Byerly, these data indicate that actin depolymerization reduces $Ca^{2+}$ influx induced by glutamate and membrane depolarization. Moreover, actin depolymerization abrogates the $[Ca^{2+}]_i$-destabilizing actin of Aβ. The suppressive effect of cytochalasin D on glutamate-induced elevation of $[Ca^{2+}]_i$ was more pronounced with increasing concentrations of glutamate (FIG. 1D). Whereas the reduction in peak $[Ca^{2+}]_i$ response was only approximately 60 nM in neurons exposed to 10 μM glutamate, the reductions were approximately 170 and 460 nM in neurons exposed to 50 and 100 μM glutamate, respectively (FIG. 1D).

EXAMPLE 6

Kainate Lesion Paradigm

A kainate lesion paradigm was employed in adult rats to determine whether cytochalasin D was also excitoprotective. Twenty-four adult male Sprague-Dawley rats (250–300 g) were divided into the indicated experimental groups (4–5 rats/group). Kainate (0.5 82 g/0.5 ml) was injected stereotaxically into region CA1 of the right hippocampus of anesthetized rats. Cytochalasin D (the indicated concentration in 1 μl of saline-1% DMSO) or vehicle was infused into the right lateral ventricle during a 5–10 min period immediately following kainate injection. Rats were killed 48 hr later and perfused transcardially with 4% paraformaldehyde. Brain sections (30 μm) were stained with cresyl violet and stained neurons in three adjacent 40X microscope fields of hippocampal region CA3 were counted (5 sections/rat). The neuronal counts were performed in sections removed approximately 200–400 μm from the injection site. This method results in highly reproducible, 75–99%, neuronal loss in the CA3 region in over 99% of the rats injected with kainate (calculations based on 302 rats receiving intrahippocampal kainate). Stereotaxic injection of a convulsant dose of kainate into region CA1 of the hippocampus resulted in selective damage to neurons in region CA3 evident 48 hr following administration (FIG. 2). Infusion of cytochalasin D into the lateral ventricles immediately following injection of kainate resulted in a highly significant reduction in neuronal injury to CA3 neurons which was related to the dose of cytochalasin D (FIG. 2). Approximately 80% of the neurons were killed by kainate in control animals receiving an intracerebroventricular infusion of saline immediately following kainate administration.

The present data indicate that the cytoskeleton plays an active role in modulating potentially neurotoxic elevations of $[Ca^{2+}]_i$ and demonstrates that compounds that affect actin polymerization prove useful in alleviating neuronal injury and death in a variety of neurodegenerative conditions.

EXAMPLE 7

Figure 3:
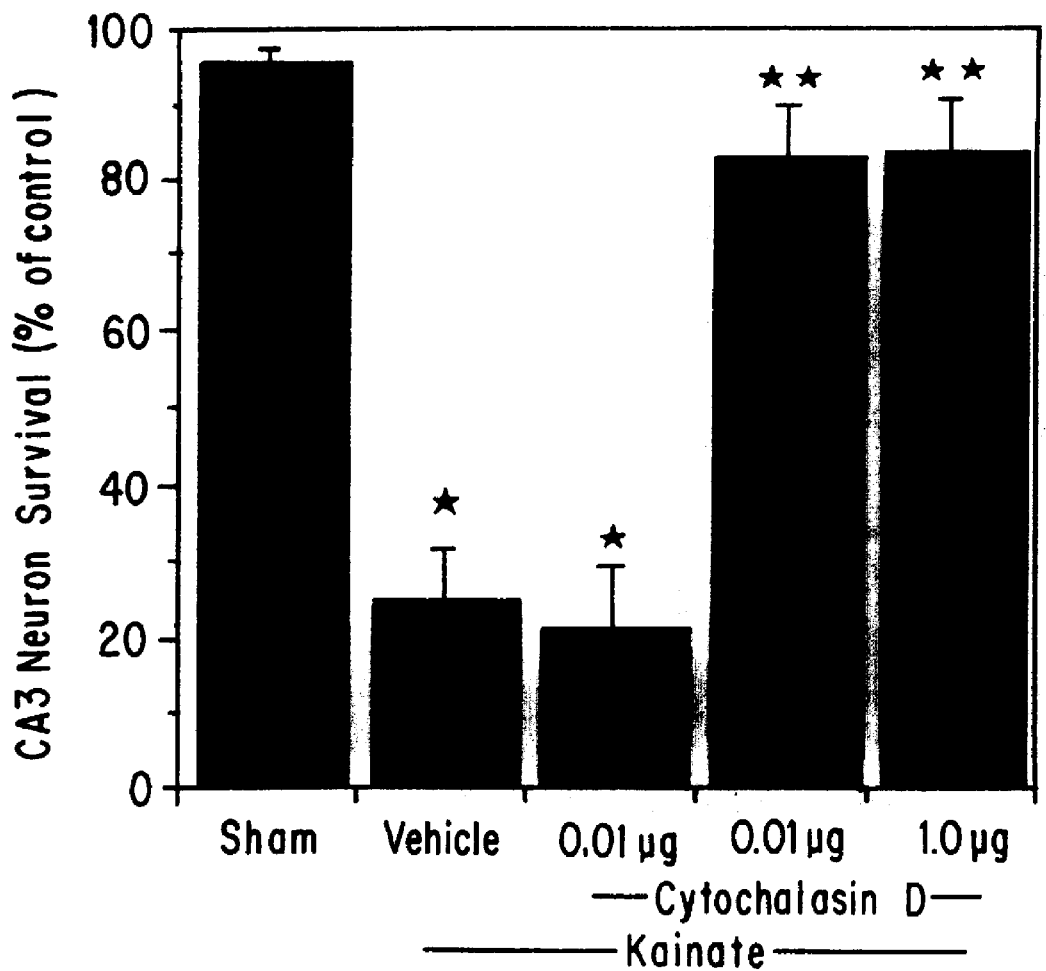
FIG. 3 shows counts of viable neurons were made in region CA3 of Sham operated rats, and rats infused intravtricularly with vehicle or increasing concentrations of cytochalasin D prior to unilateral kainate injection into region CA1 of the hippocampus.
Figure 4A:
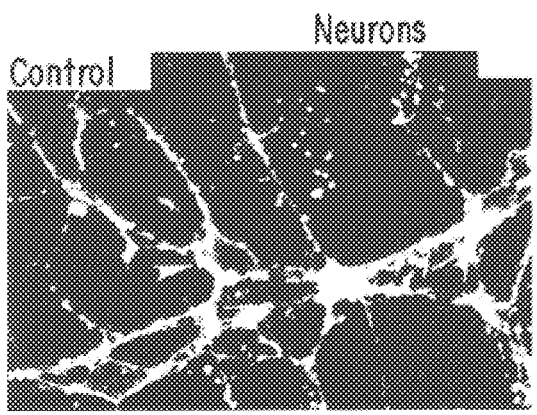
FIGS. 4A–4E show the effects of cytochalasin D and glutamate on actin filaments in cultured hippocampal cells.
Figure 4B:
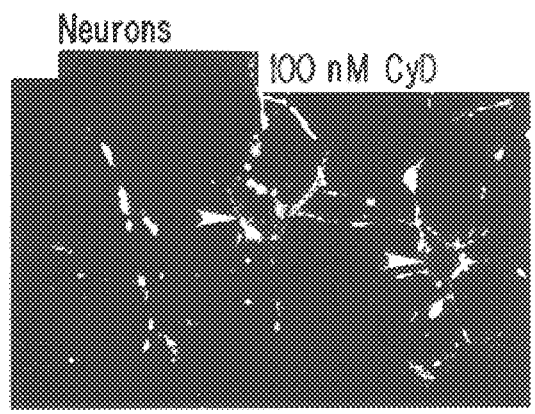
Figure 4C:
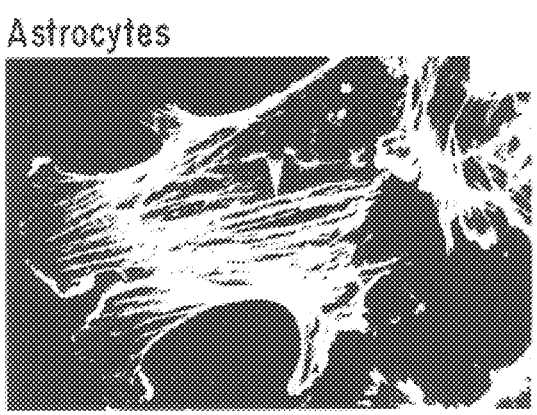
Figure 4D:
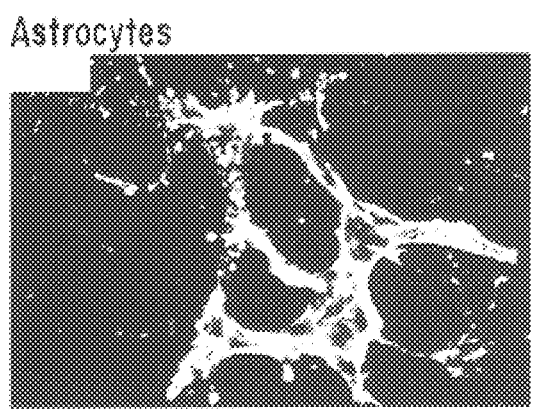
Figure 4E:
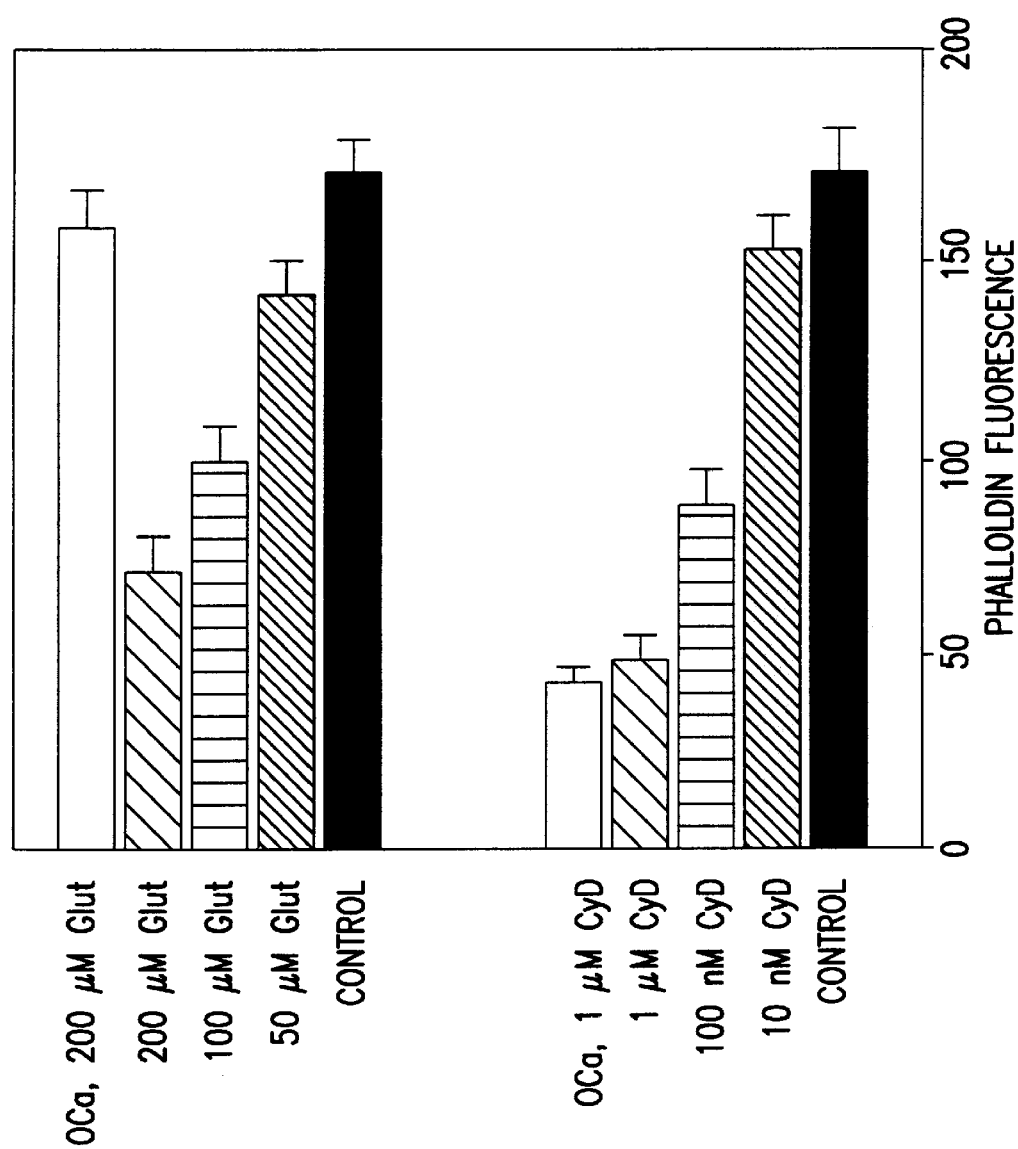

Intraventricular infusion of cytochalasin D immediately following injection of kainate resulted in a highly significant reduction in neuronal injury to CA3 neurons which was related to the dose of cytochalasin D (FIG. 3). Only 20% of the neurons were damaged by kainate in rats receiving 0.1 or 1.00 μg of cytochalasin D.

EXAMPLE 8

Cytochalasin D (10–1000 nM) caused a concentration-dependent reduction in phalloidin staining in neurons and loss of actin stress fibers in astrocytes, demonstrating its predicted disruptive effect on microfilaments (FIG. 4). Exposure of cultured neurons to increasing concentrations of glutamate also resulted in a concentration-dependent reduction in levels of phalloidin fluorescence (FIG. 4B). Glutamate did not reduce phalloidin staining in cultures incubated in $Ca^{2+}$-free medium indicating that $Ca^{2+}$ influx was required for the actin-depolymerzing action of glutamate (FIG. 4B).

EXAMPLE 9

Figure 5A:
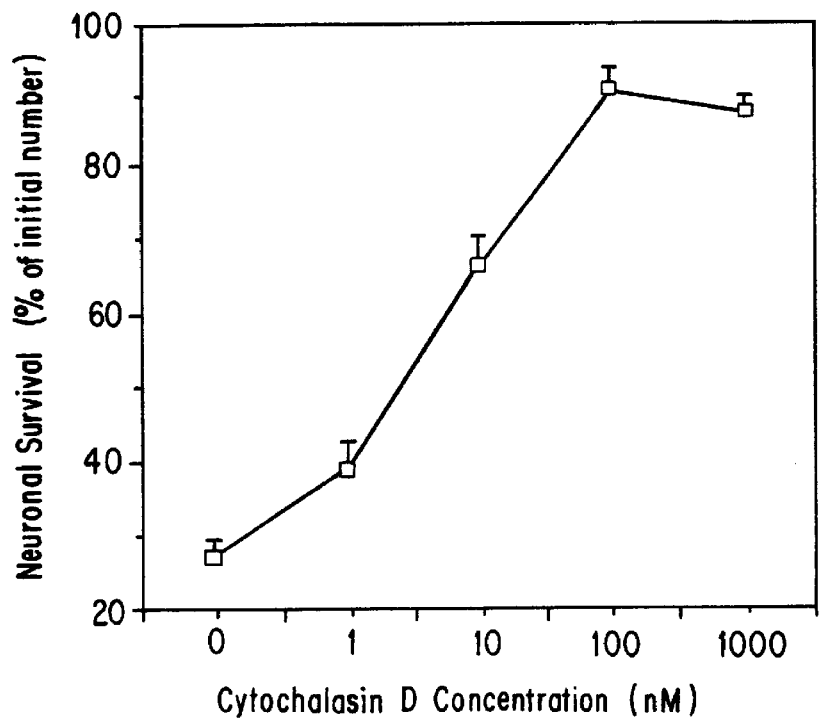
FIGS. 5A and 5B show that cytochalasin D protects cultured hippocampal neurons against glutamate toxicity.
Figure 5B:
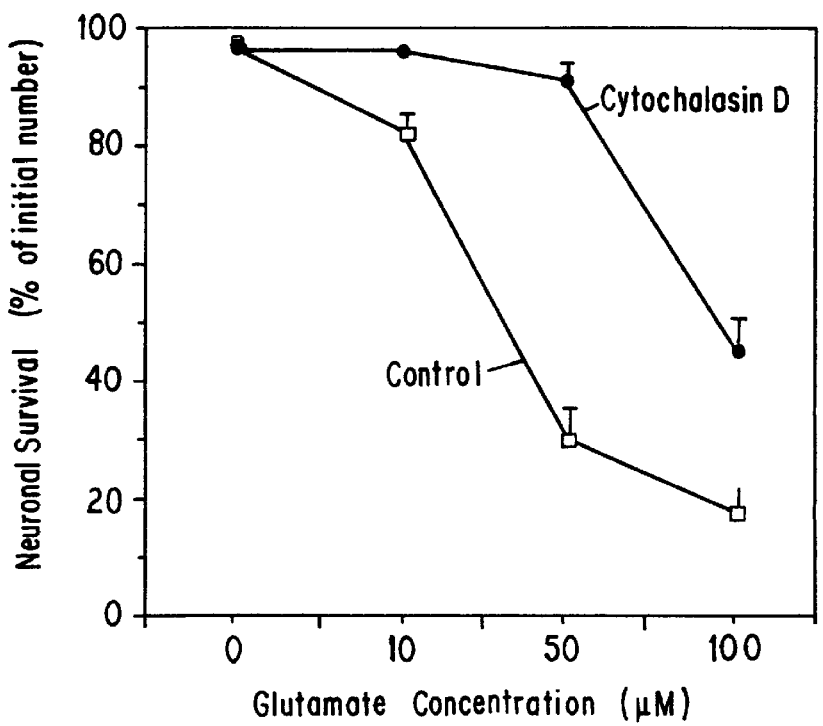

Glutamate caused a dose-dependent reduction in neuronal survival during a 20-h exposure period with a maximum killing of over 80% of the neurons with a glutamate concentration of 100 μM and an $ED_{50}$ of approximately 35 μM (FIG. 5A). Exposure of cultures to cytochalasin D (1–1000 nM) prior to exposure to glutamate resulted in a highly significant dose-dependent increase in neuronal survival compared to parallel control cultures exposed to glutamate (FIG. 5A). The concentrations of cytochalasin D that were most effective in protecting neurons against glutamate toxicity were 10 and 100 nM, with higher concentrations not providing a further increase in neuronal survival. The protection against glutamate neurotoxicity afforded by cytochalasin D was most striking in cultures exposed to submaximally toxic concentrations of glutamate (e.g., 50 μM; FIG. 5B). Whereas 50 μM glutamate killed over 70% of the neurons in control cultures, fewer than 10% were killed in cultures pretreated with 100 nM cytochalasin D and then exposed to 50 μM glutamate (FIG. 5B). Cytochalasin D (10–100 nM) alone had no significant effect on neuronal survival during a 20-h exposure period (FIG. 5B).

EXAMPLE 10

Figure 6A:
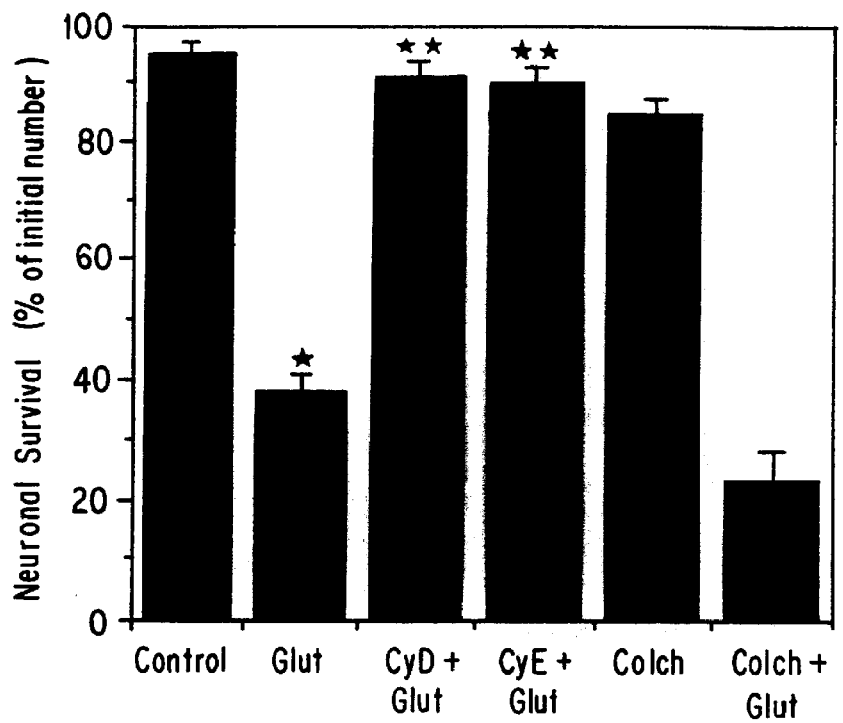
FIGS. 6A and 6B show that depolymerization of actin filaments is excitoprotective.
Figure 6B:
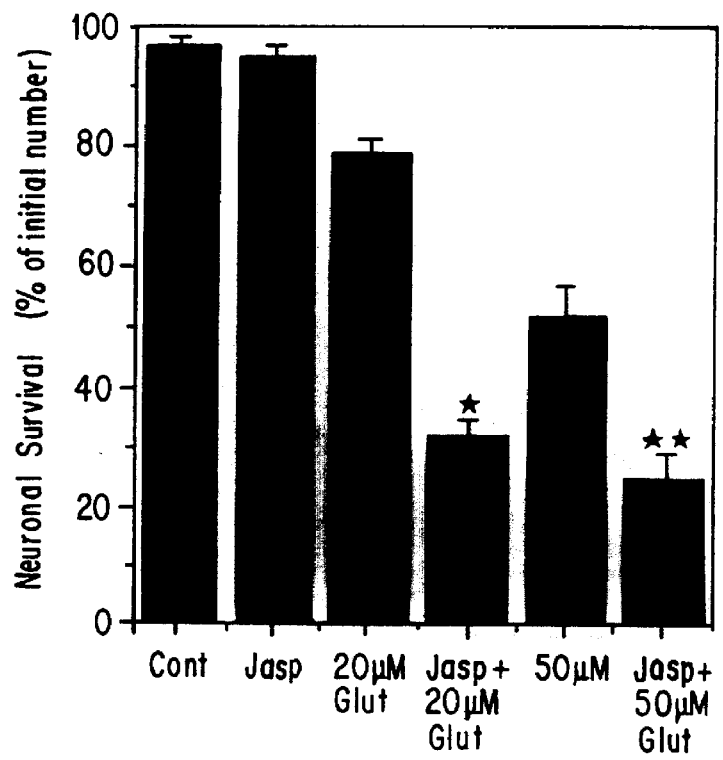

Cytochalasin E also afforded significant protection against glutamate toxicity (FIG. 6A). The microtubule-disrupting agent colchicine did not protect neurons against glutamate toxicity (FIG. 6A), indicating that cytoskeletal disruption, in general, is not excitoprotective. If actin depolymerization was excitoprotective, then exposure of neurons to an agent that blocks microfilament depolymerization should increase vulnerability to glutamate toxicity. In order to test this prediction cultures were preincubated for 3 h in the presence of 10 μM jasplakinolide, a cyclic peptide which promotes actin polymerization, and then exposed to glutamate. Glutamate neurotoxicity was significantly potentiated in cultures treated with jasplakinolide (FIG. 6B), indicating that neurons are more vulnerable to excitotoxicity under conditions in which actin depolymerization does not occur.

EXAMPLE 11

Figure 7:
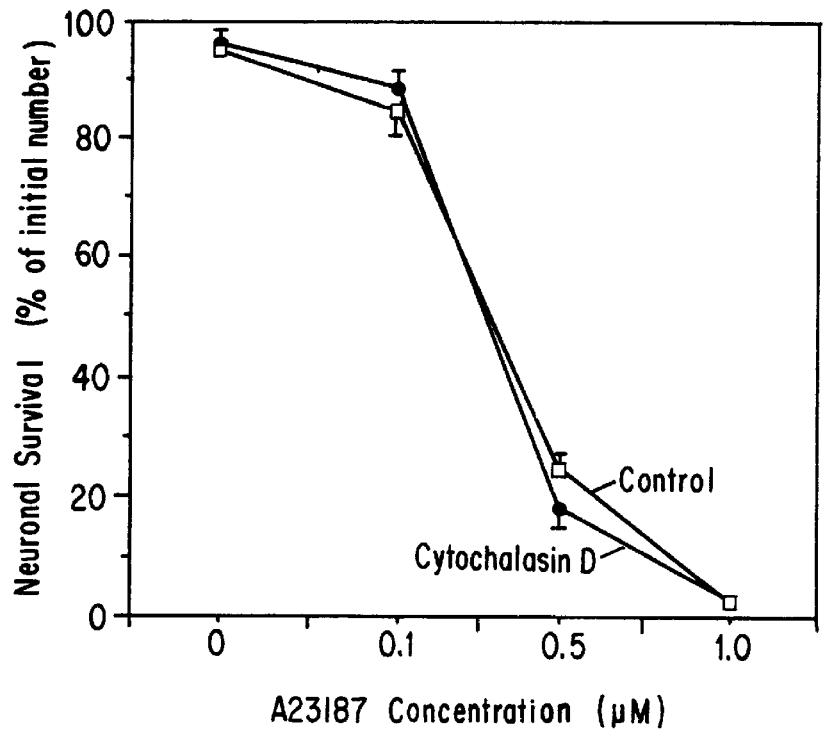
FIG. 7 shows that cytochalasin D does not protect hippocampal neurons against calcium ionophore toxicity.

Exposure of hippocampal cultures to increasing concentrations of A23187 resulted in a concentration-dependent reduction in neuronal survival (100–1000 nM) with essentially all neurons being killed by 1 μM A23187 (FIG. 7). The concentration-response curve for A23187 neurotoxicity in cultures pretreated with 100 nM cytochalasin D was essentially identical to that in control cultures, indicating that actin depolymerization was ineffective in protecting neurons against a $Ca^{2+}$ mediated insult that does not involve $Ca^{2+}$ influx through endogenous plasma membrane ion channels.

EXAMPLE 12

Figure 8:
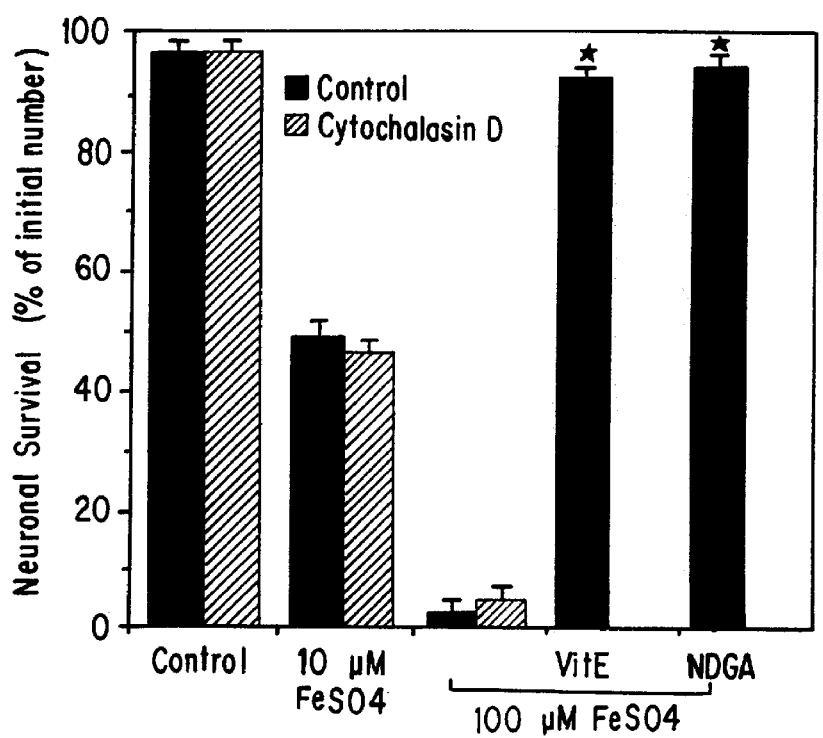
FIG. 8 shows that cytochalasin D does not protect cultured hippocampal neurons against iron toxicity.

Exposure of hippocampal cultures to increasing concentrations of $FeSO_4$ (10–100 nM) resulted in a concentration-dependent loss of neurons (FIG. 8). Neuronal loss induced by iron was not significantly altered in cultures pre-treated with 100 nM cytochalasin D, suggesting that the mechanism whereby cytochalasins protected against excitotoxicity did not involve an antioxidant effect. In contrast to cytochalasin D, two well-known antioxidants, vitamin E and nordihydroguaiaretic acid completely blocked the neurotoxicity of iron (FIG. 8).

EXAMPLE 13

Figure 9:
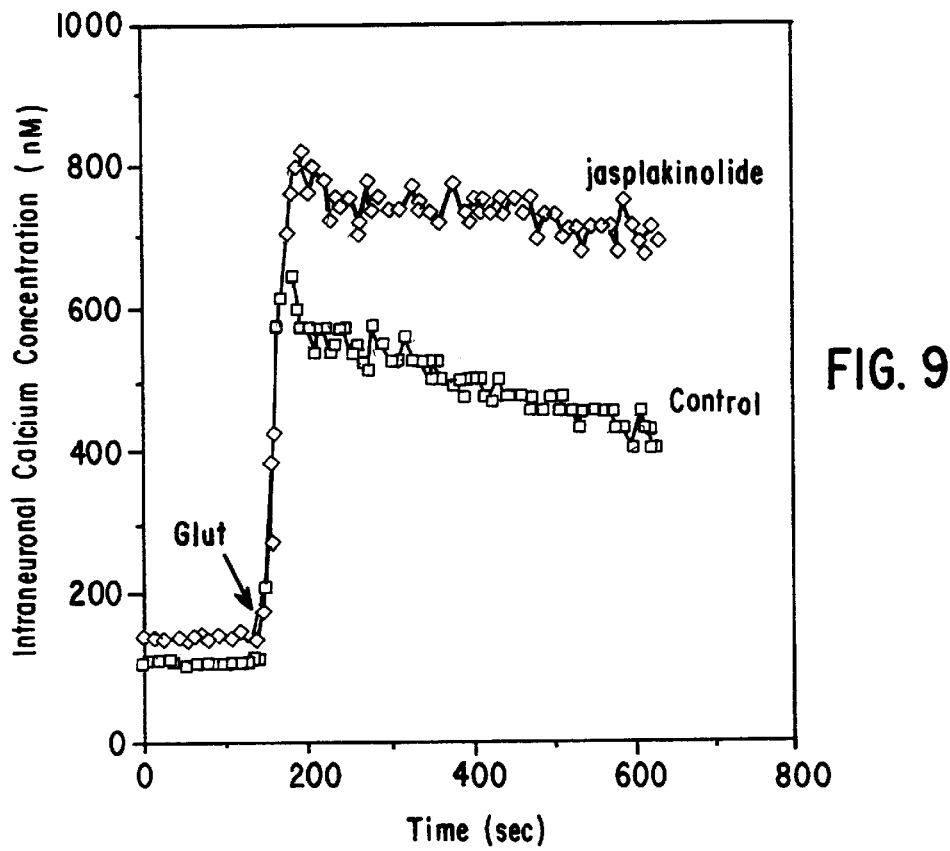
FIG. 9 shows that jasplakinolide, an actin filament-stabilizing agent, potentiates glutamate-induced elevation of $[Ca^{2+}]$ in cultured hippocampal neurons.

In order to determine whether glutamate-induced disruption of actin filaments was involved in reducing $[Ca^{2+}]_i$ responses to glutamate, cultures were pretreated with the actin filament-stabilizing agent jasplakinolide and then exposed to glutamate. Glutamate-induced elevation of $[Ca^{2+}]_i$ was potentiated in neurons pretreated with jasplakinolide compared to control cultures (FIG. 9)

EXAMPLE 14

In contrast to its ability to suppress glutamate-induced elevation of $[Ca^{2+}]_i$, cytochalasin D did not attenuate the $[Ca^{2+}]_i$ response to 500 nm calcium ionophore A23187 (FIG. 10), suggesting that actin depolymerization specifically affects influx through plasma membrane channels as opposed to enhancement of $Ca^{2+}$ extrusion or buffering. Colchicine (100 nM) did not attenuate $[Ca^{2+}]_i$ responses to glutamate.

EXAMPLE 15

Figure 11A:
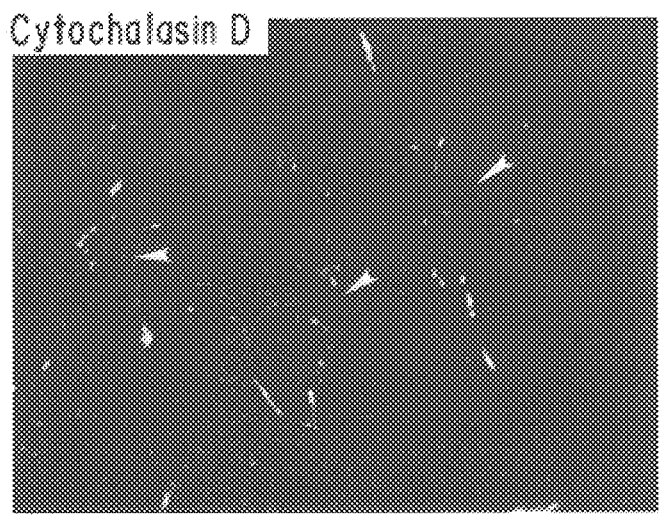
FIGS. 11A and 11B show the effects of cytochalasin D on actin filaments in cultured hippocampal cells.
Figure 11B:
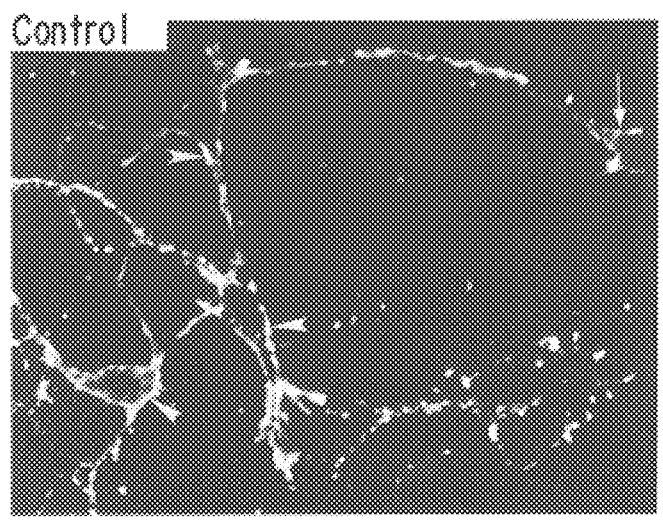

Cells were exposed to 100 nM cytochalasin D for 1 h, membranes were permeabilized, and then cells were stained with fluorescein-labeled phalloidin. Cells were examined by confocal laser scanning microscopy and images of optical sections through neurons are shown in FIG. 11. In control cultures not exposed to cytochalasin D, intense phalloidin fluorescence was present in neurons where it appeared to be concentrated in the vicinity of the plasma membrane. In addition, growth cones stained intensely with phalloidin. Cytochalasin D caused a pronounced reduction in phalloidin staining in neurons, indicating loss of actin filaments (FIG. 11).

EXAMPLE 16

Figure 12A:
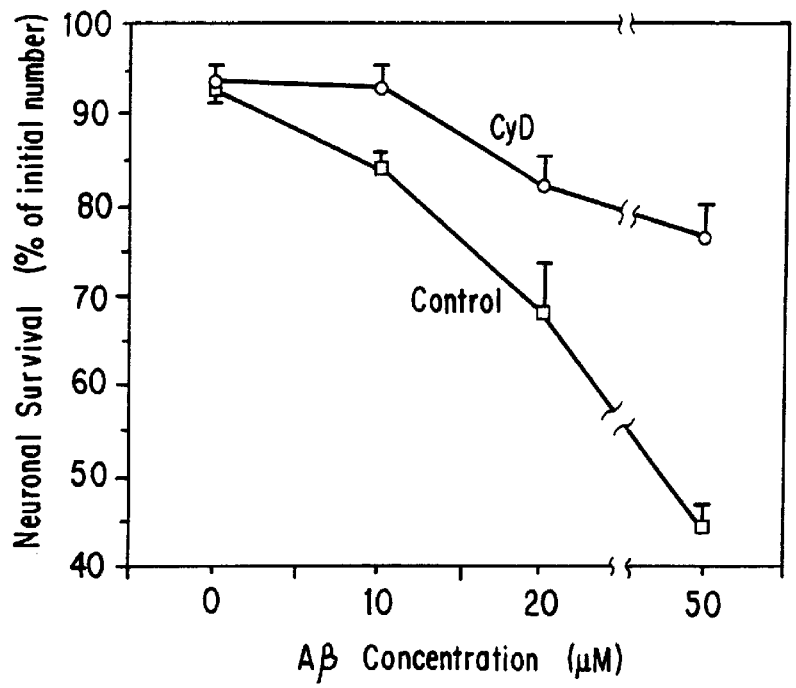
FIGS. 12A and 12B show that cytochalasin D protects cultured hippocampal neurons against Aβ toxicity.
Figure 12B:
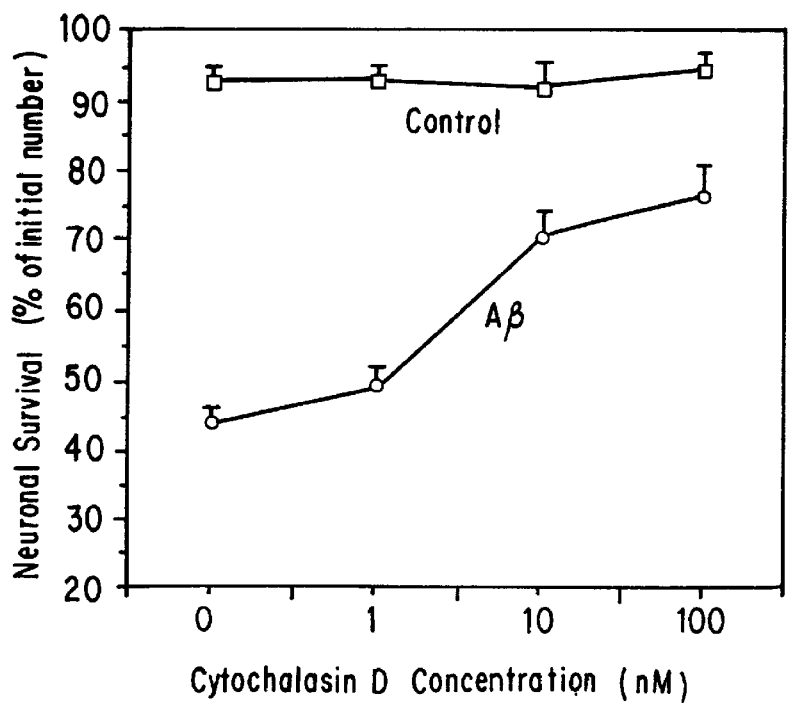

Exposure of cultured rat hippocampal neurons to increasing concentrations of Aβ25–35 resulted in a concentration-dependent reduction in neuronal survival during a 24-h incubation period (FIG. 12A). Aβ neurotoxicity was significantly attenuated in parallel cultures pretreated with 100 nM cytochalasin D. The amount of protection against Aβ neurotoxicity conferred by cytochalasin D was related to the concentration of cytochalasin D used. Significant protection occurred with 10 and 100 nM cytochalasin (FIG. 12B).

EXAMPLE 17

Figure 13:
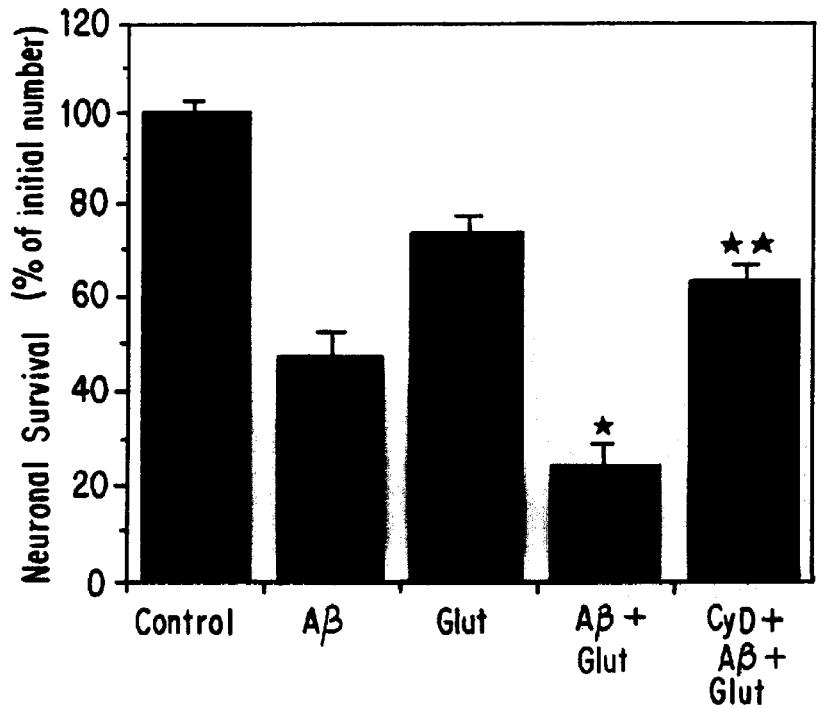
FIG. 13 shows that neurotoxicity induced by combined exposure to Aβ and glutamate is attenuated by cytochalasin D.

Exposure of neurons to both Aβ and glutamate resulted in significantly more neuronal death than in cultures exposed to either insult alone (FIG. 13). Cytochalasin D attenuated significantly neurotoxicity induced by combined exposure to Aβ and 20 μM glutamate (FIG. 13).

EXAMPLE 18

Figure 14:
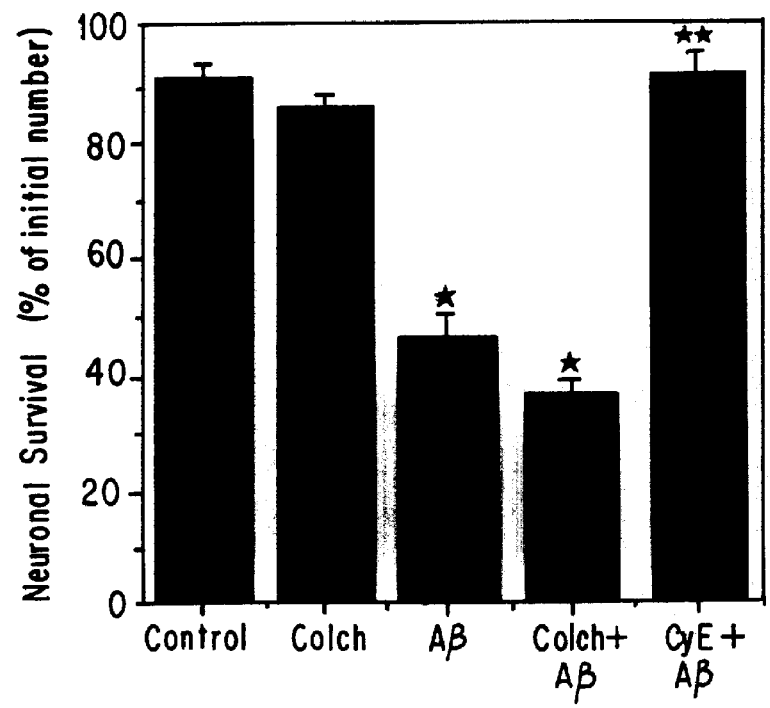
FIG. 14 Shows that cytochalasin E protection against Aβ toxicity is specific for actin-disrupting agents.

Cytochalasin E, another member of the cytochalasin family that selectively disrupts actin, attenuated Aβ neurotoxicity significantly (FIG. 14). In contrast, the microtubule-disrupting agent colchicine, at a concentration known to disrupt microtubules, did not protect neurons against Aβ toxicity (FIG. 14).

EXAMPLE 19

Figure 15:
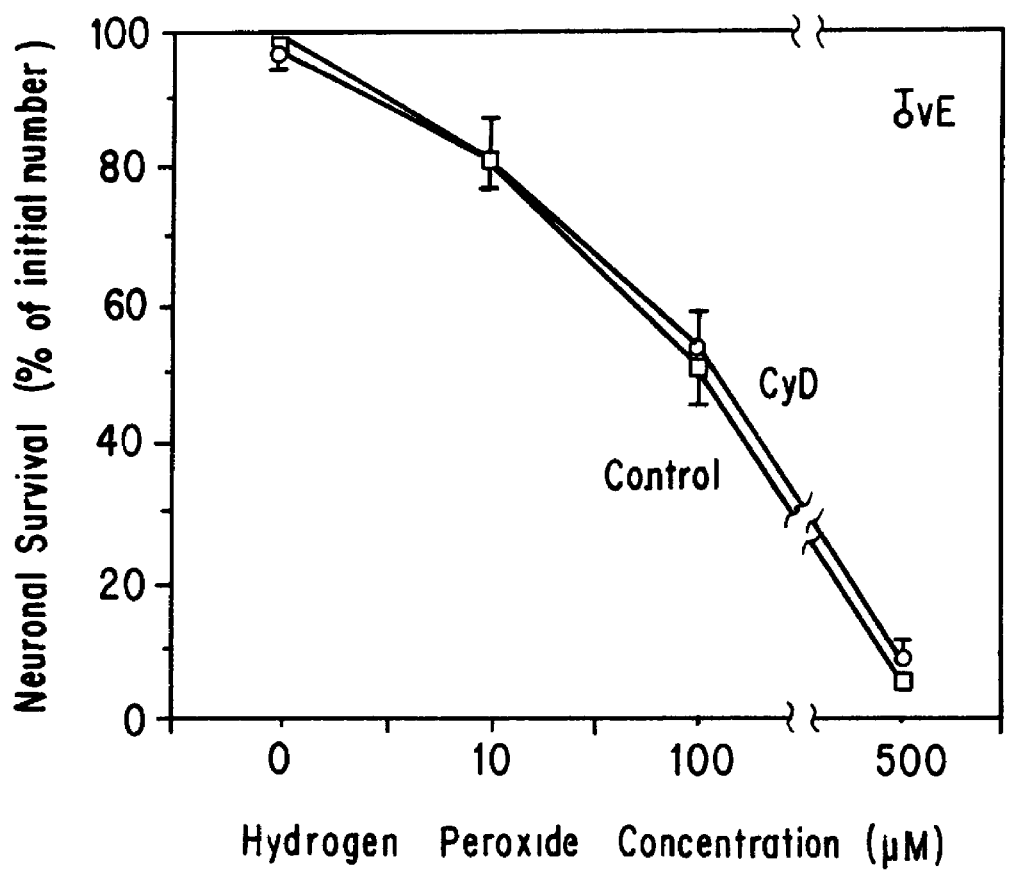
FIG. 15 shows that cytochalasin D does not protect neurons against hydrogen peroxide toxicity.

Exposure of hippocampal cultures to increasing concentrations of hydrogen peroxide resulted in a concentration-dependent reduction in neuronal survival during a 20-h exposure period (FIG. 15). Neuronal killing by hydrogen peroxide was not altered in cultures pretreated with 100 nM cytochalasin D, suggesting that this cytochalasin had little or no antioxidant activity. The neurotoxicity of hydrogen peroxide was largely prevented by pretreating cultures with the antioxidant vitamin E (FIG. 15), indicating that the toxicity of hydrogen peroxide was mediated largely by reactive oxygen species.

EXAMPLE 20

Figure 16A:
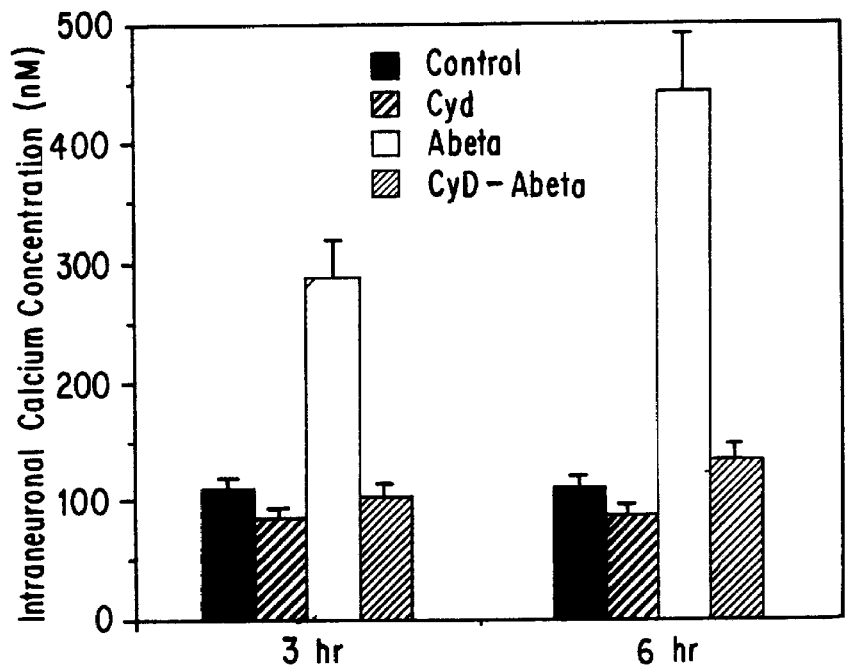
FIGS. 16A and 16B show that cytochalasin D attenuates Aβ-induced elevation of rest $[Ca^{2+}]$ and potentiation of $[Ca^{2+}]$ response to glutamate in cultured hippocampal neurons.
Figure 16B:
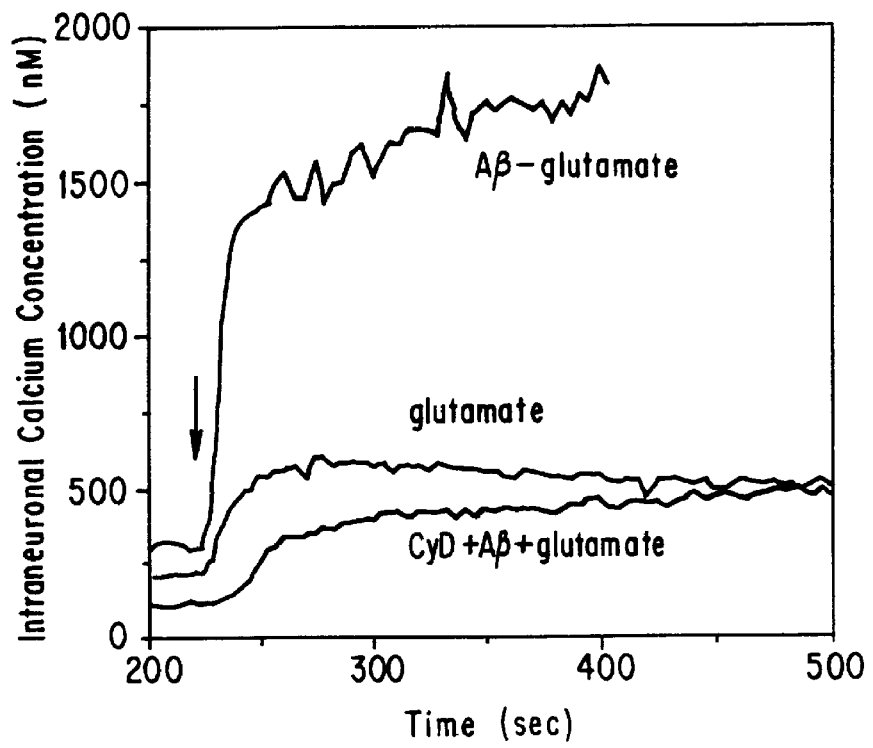

In control cultures, rest $[Ca^{2+}]_i$ was ~100 nM (FIG. 16A). Exposure of hippocampal cultures to 50 μM Aβ resulted in a significant increase in rest $[Ca^{2+}]_i$ to ~280 nM after 3 h of exposure and ~440 nM after 6 h (FIG. 16A) In parallel cultures pretreated with 100 nM cytochalasin D for 1 h and then exposed to 50 μM Aβ for 3 and 6 h., the rest $[Ca^{2+}]_i$ was not significantly elevated (FIG. 16A). We therefore determined whether cytochalasin D would affect the enhancement of $[Ca^{2+}]_i$ responses to glutamate in neurons pretreated with Aβ. As expected, the neuronal $[Ca^{2+}]_i$ response to glutamate (50 μM) was greatly enhanced in cultures pretreated with Aβ for 3 h; $[Ca^{2+}]_i$ rose rapidly to >1,500 nM compared with an increase to ~600 nM in neurons in untreated control cultures (FIG. 16B) Cytochalasin D suppressed the Aβ-induced enhancement of the $[Ca^{2+}]_i$ response to glutamate. In contrast to its ability to suppress $[Ca^{2+}]_i$ responses to Aβ and glutamate, cytochalasin D did not attenuate the $[Ca^{2+}]_i$ response to 500 nM calcium ionophore A23187 (data not shown), suggesting that the major action of cytochalasin D was a reduction in calcium influx rather than an enhancement of calcium extrusion or buffering.

DETAILED DESCRIPTION OF THE DRAWINGS

FIG. 1. Cytochalasin D attenuates $[Ca^{2+}]_i$ represents a glutamate, Aβ, and membrane depolarization in cultured hippocampal neurons.

(A) Cultures were pretreated for 1 hr with 100 nM cytochalasin D and then $[Ca^{2+}]_i$ in neurons was monitored prior to and following exposure to 50 μM glutamate. The records represent the mean $[Ca^{2+}]_i$ in 8–12 neurons. Similar results were obtained in 4 separate experiments.

(B) Aβ-induced potentiation of $[Ca^{2+}]_i$ response to glutamate is abrogated by cytochalasin D. Cultures were left untreated (Control) or were exposed to 20 μM Aβ25–35 for 6 hr or cytochalasin D plus Aβ25–35 for 6 hr. The $[Ca^{2+}]_i$ was then monitored prior to following exposure to 50 μM glutamate. Values represent the means of 8–14 neurons. Similar results were obtained in 3 separate experiments.

(C) Cultures were pretreated for 3 hr with 50 μM Aβ alone or in combination with 100 nM cytochalasin D. The $[Ca^{2+}]_i$ in neurons was then monitored prior to and following exposure to 50 mM KCl. Values represent the mean of 14–23 neurons. Similar results were obtained in a separate experiment.

(D) Cultures were pretreated for 1 h with 100 nM cytochalasin D. The $[Ca^{2+}]_i$ in neurons was measured immediately prior to, and at 5 min following, exposure to the indicated concentrations of glutamate. Values represent the means and SEM of determinations made in 17–26 neurons. *P<0.05 (10 μM glutamate), P<0.02 (50 μM glutamate), P<0.01 (100 μAM glutamate) compared to corresponding control values.

FIG. 2. Cytochalasin D protects hippocampal neurons against kainate toxicity in vivo.

Cresyl violet-stained coronal sections from brains of rats administered kainate alone (left) of kainate plus cytochalasin D (CyD; right). Note damage to CA3 neurons induced by kainate, and marked reduction in the damage in the rat receiving cytochalasin D (arrows). Lower micrographs are high magnification of a region of CA3 from the sections shown in the upper panels.

FIG. 3. Counts of viable neurons were made in region CA3 of Sham-operated rats, and rats infused intraventricularly with vehicle or increasing concentration of cytochalasin D prior to unilateral kainate injection into region CA1 of the hippocampus. Neuronal survival in the kainate injected hippocampus is expressed as a percentage of neurons in the contralateral hippocampus. Values represent the mean and SEM (4 or 5 rats/group). *p<0.01 compared to value for sham rats. **p<0.01 compared to value for vehicle-infused rats. (ANOVA with Scheffe's post-hoc test).

FIG. 4. (A) Micrographs are confocal laser scanning microscope images of cultured hippocampal cells stained with fluorescein-labeled phalloidin. Cells were exposed for 3 h to either vehicle (control; left) or 100 nM cytochalasin D (right) prior to staining with phalloidin. The top micrographs show several neurons (arrowheads point to neuronal cell bodies); note reduction in phalloidin fluorescence in cytochalasin-treated neurons. The bottom micrographs show astrocytes; note intense staining of stress fibers in control astrocytes (e.g., arrowhead) and loss of stress fibers and cell rounding in cytochalasin-treated astrocytes.

(B) Cytochalasin D and glutamate cause a reduction in neuronal phalloidin fluorescence. Parallel cultures were exposed to vehicle (control), cytochalasin D (10, 100, and 1000 nM), or glutamate (50, 100, and 200 μM) for 3 h. Additional cultures were incubated in $Ca^{2+}$-free medium (no added $Ca^{2+}$ plus 1 mM ETGA) and exposed to cytochalasin D or glutamate for 3 h. Cells were then fixed and stained with fluorescein-labeled phalloidin. Values represent the mean fluorescence intensity per neuronal cell body (±SEM; n=15–18). The reduction in phalloidin fluorescence in neurons exposed to increasing concentrations of cytochalasin D and glutamate were highly significant (P<0.0001 by ANOVA).

FIG. 5. Cultures were exposed to the indicated treatments for 20 h. Cytochalasin D was added to cultures 30 min prior to exposure to glutamate, and control cultures were exposed to 0.2% dimethylsulfoxide.

(A) Neuronal survival was quantified in cultures that had been pretreated with the indicated concentrations of cytochalasin D and then exposed to 50 μM glutamate for 20 h. Values represent the means and SEM of determinations made in four separate cultures. The overall effect of cytochalasin D in increasing neuronal survival was highly significant (P<0.0001 by ANOVA) . Pairwise statistical comparisons of cytochalasin-treated cultures with the control survival (Scheffe's test) indicated 1 nM cytochalasin D, P<0.05; 10 nM cytochalasin D, P<0.001; 100 and 1000 nM cytochalasin D, P<0.0001.

(B) Neuronal survival was quantified in cultures that had been pretreated with either vehicle (control) or 100 nM cytochalasin D and then exposed to the indicated concentrations of glutamate for 20 h. Values represent the means and SEM of determinations made in four separate cultures. Neuronal survival was significantly greater in cultures pretreated with cytochalasin D and exposed to 10 μM glutamate (P<0.05), 50 μM glutamate (P<0.001), and 100 μM glutamate (P<0.02). ANOVA with Scheffe's post hoc test.

FIG. 6. (A) Cultures were pretreated with 100 nM cytochalasin D (CyD), 100 nM cytochalasin E (CyE), or 100 nM colchicine (Colch). Cultures were then exposed to 50 μM glutamate for 20 h. Values for neuronal survival represent the means and SEM of determinations made in four separate cultures. *P<0.001 compared to control value. **P<0.001 compared to value for cultures exposed to glutamate alone.

(B) Cultures were pretreated for 1 h with 5 μM jasplakinolide or vehicle and then exposed for 20 h to the indicated concentrations of glutamate. Values represent the means and SEM of determinations made in four separate cultures. *P<0.01 compared to value for cultures exposed to 20 μM glutamate alone. **P<0.05 compared to cultures exposed to 50 μM glutamate alone.

FIG. 7. Cultures were pretreated for 1 h with 0.2% dimethylsulfoxide (control) or 100 nM cytochalasin D. Calcium ionophore A23187 was then added at the indicated concentrations and neuronal survival was assessed 8 h later. Values represent the means and SEM of determinations made in four separate cultures.

FIG. 8. Cultures were preincubated 1 h in the presence of 0.5% dimethylsulfoxide (control), 100 nM cytochalasin D, 50 μg/ml vitamin E (VitE), or 2 μM nordihydroguairetic acid (NDGA). Cultures were then exposed for 6 h to the indicated concentrations of $FeSO_4$ and neuronal survival was quantified. Values represent the means and SEM of determinations made in four separate cultures. *P<0.001 compared to value for cultures exposed to 100 μM $FeSO_4$ alone.

FIG. 9. Cultures were pretreated for 3 h with vehicle (control) or 10 μM jasplakinolide. The $[Ca^{2+}]_i$ was monitored prior to and following exposure to 50 μM glutamate. Values represent the mean of determinations made in 10–12 neurons. Similar results were obtained in two additional experiments.

Figure 10:
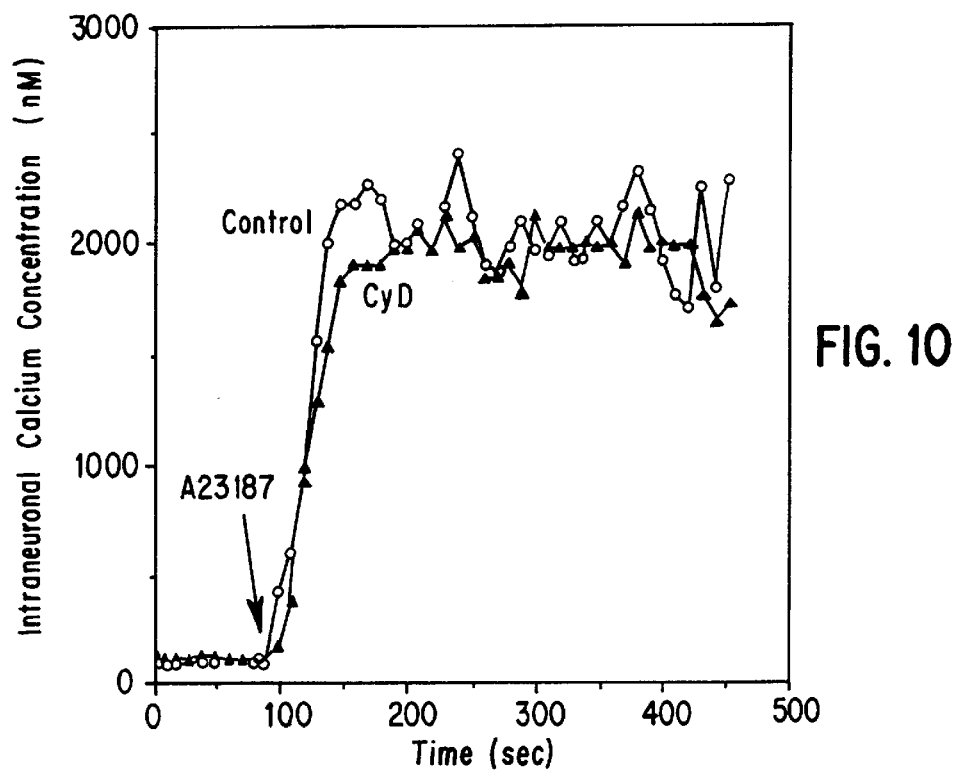
FIG. 10 shows that a cytochalasin D does not affect $[Ca^{2+}]$ responses to calcium ionophore.

FIG. 10. Cytochalasin D does not affect $[Ca^{2+}]_i$ responses to calcium ionophore. Cultures were pretreated with 100 nM cytochalasin D or vehicle (control). The $[Ca^{2+}]_i$ in neurons was then monitored prior to and following exposure to 500 nM calcium ionophore A23187. Values represent the mean of 12–20 neurons. Similar results were obtained in a separate experiment.

FIG. 11. Micrographs are confocal laser scanning microscope images of cultured hippocampal cells stained with fluorescein-labeled phalloidin. Cells were exposed for 1 h to either vehicle (Control) or 100 nM cytochalasin D before fixation and staining with FITC-phalloidin. Each panel shows several neurons. Note intense fluorescence in peripheral regions of cell bodies (e.g., arrowheads) and in growth cones (arrow) in control cultures and loss of fluorescence in cytochalasin-treated neurons (arrowheads point to edge of neuronal cell bodies).

FIG. 12. (A) Cultures were pretreated for 1 h with vehicle 0.2% dimethyl sulfoxide (Control) or 100 nM cytochalasin D (CyD) and were exposed to the indicated concentrations of Aβ25–35 for 48 h. Data are mean and SEM values of determinations made in four separate cultures. Neuronal survival was significantly increased in cytochalasin D-treated cultures exposed to 20 μM Aβ (p<0.05) and 50 μM Aβ (p<0.01).

(B) Cultures were pretreated for 1 h with the indicated concentrations of cytochalasin D and then exposed to 50 μM Aβ25–35; parallel cultures were exposed to cytochalasin D alone (Control). Data are mean and SEM values of determinations made in four separate cultures. Neuronal survival was significantly increased in Aβ-treated cultures exposed to 10 or 100 nM cytochalasin D (p<0.01).

FIG. 13. Cultures were exposed to 50 μM Aβ alone; 20 μglutamate alone; 50 μM Aβ plus 20 μM glutamate; or 100 nM cytochalasin D plus 50 μM Aβ plus 20 μM glutamate. Neuronal survival was assessed 48 h after treatment. Data are mean and SEM values of determinations made in four separate cultures. *p<0.05, compared with value for cultures exposed to Aβ alone; and p<0.01, compared with cultures exposed to glutamate alone. **p<0.01, compared with value for cultures exposed to Aβ plus glutamate.

FIG. 14. Cultures were exposed to 100 nM colchicine; 50 μM Aβ; 100 nM colchicine plus 50 μM Aβ; 100 nM cytochalasin E (CyE) plus Aβ (colchicine and cytochalasin E were added 1 h before Aβ); neuronal survival was assessed 48 h later. Data are mean and SEM values of determinations made in four separate cultures. *p<0.01, compared with values for control or colchicine alone. **p<0.01, compared with value for cultures exposed to Aβ alone.

FIG. 15. Cytochalasin D does not protect neurons against hydrogen peroxide toxicity. Cultures were pretreated for 1 h with vehicle (Control), 100 nM cytochalasin D (CyD), or 50 μg/ml vitamin E (vE) and then exposed for 20 h to the indicated concentrations of hydrogen peroxide. Data are mean and SEM values of determinations made in four separate cultures.

FIG. 16. Cytochalasin D attenuates Aβ-induced elevation of rest $[Ca^{2+}]_i$ and potentiation of $[Ca^{2+}]_i$ response to glutamate in cultured hippocampal neurons.

(A) Cultures were exposed to the indicated treatments and $[Ca^{2+}]_i$ was determined in neurons at 3 and 6 h after treatment. CyD, cytochalasin D (100 nM; added 1h before exposure to Aβ); Abeta (50 μM Aβ25–35). Data are mean and SEM values of determinations made in 17–24 neurons in three separate cultures per time point.

(B) Aβ-induced potentiation of $[Ca^{2+}]_i$ response to glutamate is abrogated by cytochalasin D. Cultures were left untreated (Control) or were exposed to 20 μM Aβ25–35 for 6 h or cytochalasin D plus Aβ25–35 for 6 h. The $[Ca^{2+}]_i$ was then monitored before and after exposure to 50 μM glutamate (glutamate was added at the time point indicated by the arrow). Data are mean values of eight to 14 neurons. Similar results were obtained in three separate experiments.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited in the bibliographic citation below are incorporated by reference in their entireties.

REFERENCES

1. Arispe, N. et al., Alzheimer disease amyloid β protein forms calcium channels in bilayer membranes: Blockade by tromethamine and aluminum. *Proc. Natl. Acad. Sci. USA* 90:567–571; 1993.
2. Bading, H. et al., Stimulation of protein tyrosine phosphorylation by NMDA receptor activation. *Science* 253:912–914; 1991.
3. Baines, A. J. In: R. D. Burgoyne (ed) *The Neuronal Cytoskeleton.* Wiley-Liss, New York, pp. 161–193 (1991).
4. Bamburg, J. R., & Bernstein, B. W. In: R. D. Burgoyne (ed) *The Neuronal Cytoskeleton.* Wiley-Liss, New York, pp. 121–160 (1991).
5. Bear, M. F. & Malenka, R. C. *Curr. Opin. Neurobiol.* 4, 389–399 (1994).
6. Behl, C. et al., Vitamin E protects nerve cells from amyloid S protein toxicity. *Biochem. Biophys. Res. Commun.* 186:944–950; 1992.
7. Bencherif, M., & Lukas, R. J. J. Neurochem. 61, 852–864 (1993).
8. Bleck, T. P., Convulsive disorders: status epilepticus. *Clin. Neuropharmacol.* 14:191–198; 1991.
9. Bonventre, J. V., Phospholipase $A_2$ and signal transduction. *J. Am. Soc. Nephrol.* 3:128–150; 1992.

10. Boxer, P. A. et al., Comparison of phenytoin with noncompetitive N-methyl-D-aspartate antagonists in a model of focal brain ischemia in rat. *Stroke* 21:III47–III51; 1990.
11. Breitner, J.C.S. et al., Inverse association of anti-inflammatory treatments and Alzheimer's disease: initial results of a co-twin control study. *Neurology* 44:227–232; 1994.
12. Busciglio, J. et al., Methodological variables in the assessment of beta amyloid neurotoxicity. *Neurobiol. Aging* 13:609–612; 1992.
13. Cai, X. D. et al., Release of excess amyloid β protein from a mutant amyloid β protein precusor. *Science* 259:514–516; 1993.
14. Cai, Z. et al., Amitriptyline, desipramine, cyproheptadine and carbamazepine, in concentrations used therapeutically, reduce kainate- and N-methyl-D-aspartate-induced intracellular $Ca^{2+}$ levels in neuronal culture. *Eur. J. Pharmacol.* 219:53–57; 1992.
15. Callazo, D., Takahashi, H., and McKay, R.D.G., Cellular targets and trophic functions of neurotrophin-3 in the developing rat hippocampus. *Neuron* 9:643–656; 1992.
16. Cantiello, H. F., Stow, J. L., Prat, A. G., & Ausiello, D. A. Actin filaments regulate epithelial Na+ channel activity. *Am. J. Physiol.* 261, C882–888 (1991).
17. Capdevila, J., et al., Inhibitors of cytochrome P450-dependent arachidonic acid metabolism. *Arch. Biochem. Biophys.* 261:257–263; 1988.
18. Chartier-Harlin, M. C. et al., Early-onset Alzheimer's disease caused by mutations at codon 717 of the β-amyloid precursor protein gene. *Nature* 353:844–846; 1991.
19. Cheng, B., and Mattson, M. P., IGF-I and IGF-II protect cultured hippocampal and septal neurons against calcium-mediated hypoglycemic damage. *J. Neurosci.* 12:1558–1566; 1992.
20. Cheng, B. et al., Glucose deprivation elicits neurofibrillary tangle-like antigenic changes in hippocampal neurons: Prevention by NGF and bFGF. *Exp. Neurol.* 117:114–123; 1992.
21. Cheng, B., Barger, S. W., and Mattson, M. P., Staurosporine, K-252a, and K-252b stabilize calcium homeostasis and promote survival of CNS neurons in the absence of glucose. *J. Neurochem.* 1994, In press.
22. Choi, D. W., Ionic dependence of glutamate neurotoxicity. *J. Neurosci.* 7:369–379; 1987.
23. Choi, D. W. Neuron 1, 623–624 (1988).
24. Citron, M. et al., Mutation of the β-amyloid precursor protein in familial Alzheimer's disease increases β-protein production. *Nature* 360:672674; 1993.
25. Clemens, J. S. et al., LY178002 reduces rat brain damage after transient global forebrain ischemia. *Stroke* 22:1048–1052; 1991.
26. Copani, A. et al., β-amyloid increases neuronal susceptibility to injury by glucose deprivation. *NeuroReport* 2:763–675; 1991.
27. DeBoni, U. et al., Controlled induction of paired helical filaments of the Alzheimer type in cultured human neurons, by glutamate and aspartate. *J. Neurol. Sci.* 68:105–118; 1985.
28. DeLorenzo, R. J., Antiepileptic Drugs, Third Edition; Raven Press, Ltd., 1989.
29. Drewes, G. et al., Mitogen activated protein (MAP) kinase transforms tau protein into an Alzheimer-like state. *EMBO J.* 11:2131–2138; 1992.
30. Dumuis, A. et al., NMDA receptors activate the arachidonic acid cascade system in striatal neurons. *Nature* 336:68–70; 1988.
31. Elliott, E. M. et al., Corticosterone kainate-induced alterations in hippocampal tau immunoreactivity and spectrin proteolysis in vivo. *J. Neurochem.* 61:57–67; 1993.
32. Evans, J. F. et al., 5-lipoxygenase-activating protein is the target of a quinoline class of leukotriene synthesis inhibitors. *Mol. Pharmacol.* 40:22–27; 1991.
33. Goate, A. et al., Segregation of a missense mutation in the amyloid precursor protein gene with familial Alzheimer's disease. *Nature* 349:704–706; 1991.
35. Goodman, Y. et al., Secreted forms of βAPP protect hippocampal neurons against Aβ toxicity and oxidative injury. *Soc. Neurosci. Abstr.,* 19:1251; 1993.
36. Goodman, Y., and Mattson, M. P., Secreted forms of βAPP protect hippocampal neurons against βpeptide-induced oxidative injury. *Exp. Neurol.* 128:1–12 (1994).
037. Greenamyre, J. T. et al., Excitatory amino acids and Alzheimer's disease. *Neurobiol. Aging* 10:593–602; 1989.
38. Grundke-Iqbal, I. et al., Abnormal phosphorylation of the microtubule-associated protein tau in Alzheimer cytoskeletal pathology. *Proc. Natl. Acad. Sci. U.S.A.* 83:4913–4917; 1986.
39. Grynkiewicz, G. et al., A new generation of $Ca^{2+}$ indicators with greatly improved fluorescence properties. *J. Biol. Chem.* 260:3440–3450; 1985.
40. Haass, C. et al., Amyloid β-peptide is produced by cultured cells during normal metabolism. *Nature* 359:322–325; 1992.
41. Hall, E. D., Novel inhibitors of iron-dependent lipid peroxidation for neurodegenerative disorders. *Ann. Neurol.* 32:S137–S142; 1992.
42. Hartmann, H. et al., β-amyloid protein amplifies calcium signalling in central neurons from the adult mouse. *Biochem. Biophys. Res. Commun.* 194:1216–1220 (1993).
43. Henriksen, O., Johannessen S. I., Clinical and pharmacokinetic observations on sodium valproate: A 5-year follow-up study in 100 children with epilepsy. *Acta Neurol. Scandinav.* 65:504–523; 1982.
44. Hensley et al., A model for β-amyloid aggregation and neurotoxicity based on free radical generation by the peptide. *Proc. Natl. Acad. Sci. U.S.A.* 91:3270–3274 (1994).
45. Herbert, J. M., Seban, E., and Maffrand, J. P., Characterization of specific binding sites for [$^3$H]-staurosporine on various protein kinases. *Biochem. Biophys. Res. Commun.* 171:189–195; 1990.
46. Hope, W. C. et al., In vitro inhibition of the biosynthesis of slow reacting substance of anaphylaxis (SRS -A) and lipoxygenase activity by quercetin. *Biochem. Pharmacol.* 32: 367–371; 1983.
47. Jesberger, J. A., and Richardson, J. S., Oxygen free radicals and brain dysfunction. *Int. J. Neurosci.* 57:1–17; 1991.
48. Johnson, B. D., & Byerly, L., A Cytoskeletal Mechanism for $Ca^{2+}$ Channel Metabolic Dependence and Inactivation by Intracellular $Ca^{2+}$, Neuron. 10, 797–804 (1993).
49. Johnson. G.V.W. et al., Degradation of microtubule-associated protein 2 and brain spectrin by calpain: a comparative study. *J. Neurochem* 56:1630–1638; 1991.
50. Kane, D. J. et al., Bcl-2 inhibition of neural death: decreased generation of reactive oxygen species. *Science* 262:1274–1277; 1993.
51. Kase, H., Iwahashi, K., Nakanishi, S., Matsuda, Y., Yamada, K., Takahishi, J., Murakata, C., Sato, A., and Kaneko, M., K-252 compounds, novel and potent inhibitors of protein kinase C and cyclic nucleotide-dependent protein kinases. *Biochem. Biophys. Res. Commun.* 142:436–440; 1987.

52. Kennedy, M. B., Regulation of neuronal function by calcium, *Trends Neurosci.* 12, 417–420 (1989).
53. Kelly, R. B. Cell/Neuron 72/10 (Suppl), 43–53 (1993).
54. Khachaturian, Z. S., The role of calcium regulation in brain agina: reexamination of a hypothesis. *Aging* 1:17–34; 1989.
55. Knusel, B., and Hefti, F., Multiple and interactive responses of central neurons to neurotrophic factors. *Semin. Neurosci.* 5:259–267; 1993.
56. Koh, J. Y. et al., β-amyloid protein increases the vulnerability of cultured cortical neurons to excitotoxic damage. *Brain Res.* 533:315–320; 1990.
57. Kosik, K. S. et al., Epitopes that span the tau molecule are shared with paired helical filaments. *Neuron* 1:817–825; 1988.
58. Lampe, H. et al., Carbamazepine blocks NMDA-activated currents in cultured spinal cord neurons. *Neuroreport* 1:26–28; 1990.
59. Lee, V. M. et al., A68: A major subunit of paired helical filaments and derivatized forms of normal tau. *Science* 251:675–678; 1991.
60. MacDonald, R. L. et al., Antiepileptic drug mechanisms of action. *Epilepsia* 34:S1–S8; 1993.
61. March, L., & Letournea, P. C. *J. Cell. Biol.* 99, 2041–2047 (1984).
62. Mark, R. J. et al., Amyloid β-peptide impairs ion-motive ATPase activities: Evidence for a role in loss of neuronal $Ca^{2+}0$ homeostasis and cell death. *J. Neurosci.* 15:6239–6249 (1995).
63. Mattson, M. P., and Kater, S. B., Isolated hippocampal neurons in cryopreserved long-term cultures: Development of neuroarchitecture and sensitivity to NMDA. Tnt. *J. Dev. Neurosci.* 6:439–452; 1988.
64. Mattson, M. P. et al., Outgrowth-regulating actions of glutamate in isolated hippocampal pyramidal neurons. *J. Neurosci.* 8:2087–2100; 1988.
65. Mattson M. P. et al., Roles for mitotic history in the generation and degeneration of hippocampal neuroarchitecture. *J. Neurosci.* 9:1223–1232; 1989.
66. Mattson, J. P. et al., Excitatory and inhibitory neurotransmitters in the generation and degeneration of hippocampal neuroarchitecture. *Brain Res.* 478:337–348; 1989.
67. Mattson et al., Fibroblast growth factor and glutamate: opposing roles in the generation and degeneration of hippocampal neuroarchitecture. *J. Neurosci.* 9:3728–3740; 1989.
68. Mattson, M. P., Antigenic changes similar to those seen in neurofibrillary tangles are elicited by glutamate and calcium influx in cultured hippocampal neurons. *Neuron* 4:105–117; 1990.
69. Mattson, M. P. et al., Effects of elevated intracellular calcium levels on the cytoskeleton and tau in cultured human cortical neurons. Mol. *Chem. Neuropathol.* 15:117–142; 1991.
70. Mattson, M. P., Effects of microtubule stabilization and destabilization on tau immunoreactivity in cultured hippocampal neurons. *Brain Res.* 582:107–118; 1992.
71. Mattson, M. P., Calcium as sculptor and destroyer of neural circuitry. *Exp. Gerontol.* 27:29–49; 1992.
72. Mattson, M. P. et al., β-amyloid peptides destabilize calcium homeostasis and render human cortical neurons vulnerable to excitotoxicity. *J. Neurosci.* 12:379–389; 1992.
73. Mattson, M. P., Kumar, K., Cheng, B., Wang, H., and Michaelis, E. K., Basic FGF regulates the expression of a functional 71 kDa NMDA receptor protein that mediates calcium influx and neurotoxicity in cultured hippocampal neurons. *J. Neurosci.* 13:4575–4588, 1993.
74. Mattson, M. P., Cheng, B., and Smith-Swintosky, V. L., Neurotrophic factor mediated protection from excitotoxicity and disturbances in calcium and free radical metabolism. *Seminars Neurosci.* 5:295–307, 1993.
75. Mattson, M. P. et al., Calcium-destabilizing and neurodegenerative effects of aggregated β-amyloid peptide are attenuated by basic FGF. *Brain Res.* 621:35–49; 1993.
76. Mattson, M. P. et al., β-Amyloid precursor protein metabolites and loss of neuronal calcium homeostasis in Alzheimer's disease. *Trends Neurosci.* 16:409–415; 1993.
77. Mattson, M. P. et al., Calcium, free radicals, and excitotoxic neuronal death in primary cell culture. *Meth. Cell Biol.* 46:187–216 (1995).
78. Matus, A., Microtubule-associated proteins: their potential role in determining neuronal morphology. *Annu. Rev. Neurosci.* 11, 29–44 (1988).
79. McDonald, J. W. et al., Pharmacology of N-methyl-Daspartate-induced brain injury in an in vivo perinatal rat model. *Synapse* 6:179–188; 1990.
80. Mehler, et al., Enhanced sensitivity of hippocampal pyramidal neurons from mdx mice to hypoxia-induced loss of synaptic transmission. *Proc. Natl. Acad. Sci. U.S.A.* 89:2461–2465; 1992.
81. Mohr, E. et al., GABA-Agonist therapy for Alzheimer's Disease. *Clinical Neuropharmacology* 9:257–263; 1986.
82. Monyer, H. et al., 21-Aminosteroids attenuate excitotoxic neuronal injury in cortical cell cultures. *Neuron* 5:121–126; 1990.
83. Mori, H. et al., Ubiquitin is a component of paired helical filaments in Alzheimer's disease. *Science* 235:1641–1644; 1987.
84. Mullan, M. et al., Genetic and molecular advances in Alzheimer's disease. *Trends Neurosci.* 16:398403; 1993.
85. Murrell, J. et al., A mutation in the amyloid precursor protein associated with hereditary Alzheimer's disease. *Science* 254:97–99; 1991.
86. Nadler, I. V., & Cuthbertson, G. J. *Brain Res.* 195, 47–56 (1980).
87. Nakanishi, S., Matsuda, Y., Iwahashi, K., and Kase, H., K-252b, c and d, potent inhibitors of protein kinase C from microbial origin. *J. Antibiot.* (Tokyo) 39:1066–1071; 1986.
88. Nilsson, M. et al., Agonist-evoked $Ca^{2+}$ transients in primary astroglial cultures—modulatory effects of valproic acid. *Glia* 5:201–209; 1992.
89. Nowak, T. S. Jr. et al., Stress protein and protooncogene expression as indicators of neuronal pathophysiology after ischemia. *Prog. Brain Res.* 96:195–208; 1993.
90. Page, B. et al., A new fluorometric assay for cytotoxicity measurements in vitro. *Int. J. Oncology* 3:473–476; 1993.
91. Perry, G. et al., Ubiquitin is detected in neurofibrillary tangles and senile plaque neurites of Alzheimer's disease. *Proc. Natl. Acad. Sci. U.S.A.* 84:3030–3036; 1987.
92. Pike, C. J. et al., In vitro aging of β-amyloid protein causes peptide aggregation and neurotoxicity. *Brain Res.* 563:311–314; 1991.
93. Pike, C. J. et al., Neurodegeneration induced by β-amyloid peptides in vitro; the role of peptide assembly state. *J. Neurosci.* 13:1676–1687; 1993.
94. Rogers, J. et al., Clinical trial of indomethacin in Alzheimer's disease. *Neurology* 43:1609–1611; 1993.
95. Ponchaut, S. et al., In vitro effects of valproate and valproate metabolites on mitochondrial oxidations. Relevance of CoA sequestration to the observed inhibitions. *Biochem. Pharmacol.* 43:2435–2442; 1992.
96. Potter, P. E. et al., Dephenylhydantoin attenuates hypoxia-induced release of $^3$H-glutamate from rat hippocampal slices. *Brain Res.* 558:127–130; 1991.

97. Rayevsky, K. S. et al., GABA-ergic drugs: effects on conditioning, memory, and learning. *Pharmacol. Res. Commun.* 15:85–96; 1983.
98. Rose, K. et al., Nordihydroguaiaretic acid potentiates rapidly triggered excitotoxic injury in murine cortical cell cultures. *Soc. Neurosci. Abstr.* 17:784; 1991.
99. Rosenkranz, A. R. et al., A microplate assay for the detection of oxidative products using 2',7'-dichlorofluorescin diacetate. *J. Immunol. Methods* 156:39–45; 1992.
100. Rosenmund, C., & Westbrook, G. L., Calcium-induced actin depolymerization reduces NMDA channel activity. *Neuron.* 10, 805–814 (1993).
101. Rothman, S., & Olney, J. W. *Ann. Neurol.* 19, 105–111 (1986).
102. Rothman, S. M. et al., Nordihydroguaiaretic acid attenuates NMDA neurotoxicity Action beyond the receptor. *Neuropharmacol.* 32:1279–1288; 1993.
103. Sapolsky, R. M., Glucocorticoids, hippocampal damage and the glutamatergic synapse. *Prog. Brain Res.* 86:13–23; 1990.
104. Sautiere P. E. et al., Tau antigenic changes induced by glutamate in rat primary culture model: a biochemical approach. *Neurosci. Lett.* 140:206–210; 1992.
105. Schubert, D. et al., Growth factors and vitamin E modify neuronal glutamate toxicity. *Proc. Natl. Acad. Sci. USA* 89:8264–8267; 1992.
106. Selkoe, D. J., The molecular pathology of Alzheimer's disease. *Neuron* 6:487–498; 1991.
107. Selkoe, D. J., Physiological production of the amyloid protein and the mechanism of Alzheimer's disease. *Trends Neurosci.* 16:403–409; 1993.
108. Seubert, P. et al., Isolation and quantitation of soluble Alzheimer's β-peptide from biological fluids. *Nature* 359:325–327; 1992.
109. Seubert, P. et al., Secretion of β-amyloid precursor protein cleaved at the amino terminus of the β-amyloid peptide. *Nature* 361:260–263; 1993.
110. Sgaragli, G. P., et al. (1993) Calcium antagonist and antiperoxidant properties of some hindered phenols. *Br. J. Pharmacol.* 110, 369–377.
111. Shoji, J. et al., Production of the Alzheimer amyloid S protein by normal proteolytic processing. *Science* 258:126–129; 1992.
112. Siman, R. et al., Excitatory amino acids activate calpain I and induce structural protein breakdown in vivo. *Neuron* 1:279–287; 1988.
113. Simmons, L. K. et al., Secondary structure of amyloid S peptide correlates with neurotoxic activity in vitro. *Mol. Pharmacol.* 1994, In press.
114. Smith, et al., Excess brain protein oxidation and enxyme dysfunction in normal aging and in Alzheimer disease. *Proc. Natl. Acad. Sci. U.S.A.* 88:10540–10543; 1991.
115. Sternlicht, H., & Ringel, I., *J. Biol. Chem.* 254, 10540–10550 (1979).
116. Steppuhn, K. G. et al., Modulation of the seizure threshold for excitatory amino acids in mice by antiepileptic drugs and chemoconvulsants. *J. Pharmacol. Exp. Ther.* 265:1063–1070; 1993.
117. Taft, W. C. et al., Phenytoin protects against ischemia-produced neuronal cell death. *Brain Res.* 483:143–148; 1989.
118. Tischler, A. S., Ruzicka, L. A., and Hobner, P. R., A protein kinase inhibitor, staurosporine, mimics nerve growth factor induction of neurotensin/neuromedia N gene expression. *J. Biol. Chem.* 266:1141–1146; 1991.
119. Ueda, K. et al., Alz-50 recognizes a phosphorylated epitope of Tau protein. *J. Neurosci.* 10:3295–3304; 1990.
120. Verity, M. A., Mechanisms of phospholipase $A_2$ activation and neuronal injury. *Ann. N.Y. Acad. Sci.* 679:110–120; 1993.
121. Wallis, R. A. et al., Protection from hypoxic and N-methyl-D-aspartate injury with azelastine, a leukotriene inhibitor. *Eur. J. Pharmacol.* 238:165–171; 1993.
122. Watanabe, Y. et al., Phenytoin prevents stress and corticosterone-induced atrophy of CA3 pyramidal neurons. *Hippocampus* 2:431–435; 1992.
123. Wolozin, B. L. et al., A neuronal antigen in the brains of Alzheimer's patients. *Science* 232:648–650; 1986.
124. Yanker, B. A. et al., Neurotrophic and neurotoxic effects of amyloid β protein: reversal by tachykinin neuropeptides. *Science* 250:279–282; 1990.
0125. Yoshimoto, T. et al., 2,3,5-trimethyl-6-(12-hydroxy-5,10-dodecadiynyl)-1,4-benzoquinone (AA861), a selective inhibitor of the 5-lipoxygenase reaction and the biosynthesis of slow-reacting substance of anaphylazis. *Biochim. Biophys. Acta* 713:470–473; 1982.
126. Zeise, M. L. et al., Valproate suppresses N-methyl-D-aspartate-evoked, transient depolarizations in the rat neocortex in vitro. *Brain Res.* 544:345–348; 1991.
127. Zhang, Y. et al., Basic FGF, NGF, and IGFs protect hippocampal and cortical neurons against iron-induced degeneration. *J. Cerebral. Blood Flow Metab.* 13:378–388; 1993.

What is claimed is:

1. A method for reducing adverse effects of a neurodegenerative disorder comprising: administering to a patient a therapeutically effective amount of at least one compound selected from the group consisting of compounds represented by Formulas (I)–(II) and their pharmaceutically acceptable salts:

(I)

where $R_1$, $R_2$, $R_3$, $R_4$, $R_5$, $R_6$, and $R_7$ represent hydrogen, $C_1$ to $C_6$ alkyl or hydroxy, or where $R_3$ and $R_4$ together represent a carbonyl group; or (II)

where $R_1$, $R_2$, $R_3$, $R_4$, $R_5$, $R_6$, $R_7$, $R_8$, and $R_9$ represent hydrogen, $C_1$ to $C_6$ alkyl, hydroxy, or OAC, or where $R_3$ and $R_4$ together represent a carbonyl group.

2. A method according to claim 1, wherein the compound is represented by formula (I) or pharmaceutically acceptable salts thereof.

3. A method according to claim 2, wherein the compound is cytochalasin D.

4. A method according to claim 1, wherein the compound is represented by formula (II) or pharmaceutically acceptable salts thereof.

5. A method according to claim 4, wherein the compound is cytochalasin E.

6. A method according to claim 1, wherein the neurodegenerative disorder is selected from the group consisting of Alzheimer's disease, Down's syndrome, amyotrophic lateral sclerosis, Parkinson's disease, Huntington's disease, cerebral ischemia, cerebral infarction, thromboembolic and hemorrhagic stroke, cerebral vasospasm, hypoglycemia, cardiac arrest, status epilepticus, perinatal asphyxia, anoxia, pulmonary surgery, and cerebral trauma.

* * * * *